(12) United States Patent
Holländer et al.

(10) Patent No.: US 7,270,953 B2
(45) Date of Patent: Sep. 18, 2007

(54) COMPOSITIONS FOR ISOLATING AND/OR STABILISING NUCLEIC ACIDS IN BIOLOGICAL MATERIAL

(75) Inventors: Vera Holländer, Unna (DE); Ralf Wyrich, Grevenbroich (DE); Uwe Oelmüller, Erkrath (DE)

(73) Assignee: Qiagen GmbH, Hilden (DE)

( * ) Notice: Subject to any disclaimer, the term of this patent is extended or adjusted under 35 U.S.C. 154(b) by 110 days.

(21) Appl. No.: 10/312,745

(22) PCT Filed: May 22, 2001

(86) PCT No.: PCT/EP01/05888

§ 371 (c)(1),
(2), (4) Date: Jun. 9, 2003

(87) PCT Pub. No.: WO02/00599

PCT Pub. Date: Jan. 3, 2002

(65) Prior Publication Data

US 2004/0014703 A1  Jan. 22, 2004

(30) Foreign Application Priority Data

Jun. 27, 2000  (DE) ................... 100 31 236

(51) Int. Cl.
*C12Q 1/68* (2006.01)
*C07H 21/00* (2006.01)
*C07H 21/04* (2006.01)
(52) U.S. Cl. .................. 435/6; 536/23.1; 536/25.4
(58) Field of Classification Search .......... 435/6; 536/25.4, 23.1

See application file for complete search history.

(56) References Cited

U.S. PATENT DOCUMENTS

| 5,010,183 A | 4/1991 | Macfarlane |
| 5,196,182 A | 3/1993 | Ryan |
| 5,260,048 A | 11/1993 | Ryan |
| 5,275,708 A | 1/1994 | Akins et al. |
| 5,300,635 A | 4/1994 | Macfarlane |
| 5,891,921 A | 4/1999 | Walker |

FOREIGN PATENT DOCUMENTS

| CA | 2299119 | 8/2000 |
| EP | 0 606 712 | 7/1994 |
| EP | 0 442 026 | 12/1995 |
| EP | 0 743 950 | 11/1996 |
| GB | 1 289 426 | 9/1972 |
| WO | WO99/29904 | 6/1999 |
| WO | WO 00/06780 | 2/2002 |

OTHER PUBLICATIONS

Schmidt et al., *J. Medical Virology*, 47: 153 (1995).

*Primary Examiner*—Jezia Riley
(74) *Attorney, Agent, or Firm*—Yankwich & Associates, P.C.; Leon R. Yankwich; Michael R. Wesolowski

(57) ABSTRACT

The present invention relates to new compositions for isolating and/or stabilising nucleic acids in materials of biological origin. The compositions comprise as an essential ingredient a cationic compound of general formula $$Y^+R_1R_2R_3R_4X^-$$

wherein
Y may represent nitrogen or phosphorus
$R_1$, $R_2$, $R_3$ and $R_4$ independently of one another may represent a branched or unbranched $C_1$-$C_{20}$-alkyl group and/or a $C_6$-$C_{20}$-aryl group as well as a $C_6$-$C_{26}$-aralkyl group and $X^-$ may represent an anion of an inorganic or organic, mono- or polybasic acid.

35 Claims, 15 Drawing Sheets

10% TTAOx/
200 mM acetic acid
pH 3
48 h RT

10% TTAOx/
200 mM succinic acid
pH 2
48 h RT

10% TTAOx/
200 mM malonic acid
pH 2
48 h RT

10% TTAOx/
200 mM glutaric acid
pH 2
24 h RT

10% TTAOx/
200 mM oxalic acid
pH 3
24 h RT

10% TTAOx/
200 mM citric acid
pH 3
24 h RT

10% TTAOx/
200 mM tartaric acid
pH 3
48 h RT

10% TTAOx/
200 mM malic acid
pH 3
24 h RT

10% TTAOx/
200 mM tartronic acid
pH 4
48 h RT

10% TTAOx/
200 mM adipic acid
pH 2
24 h RT

| RNA | Yield: | OD 260/280nm: |
|---|---|---|
| 24h | 5,1 µg | 1,94 |
|  | 5,5 µg | 1,91 |
| 48h | 6,5 µg | 1,95 |
|  | 6,2 µg | 1,92 |
| 72h | 5,9 µg | 1,94 |
|  | 7,1 µg | 1,92 |

A: GAPDH-probe storage period

B: IFN-γ probe storage period

LM= Length marker (800 ng Lambda-DNA cut with Hind III

Yield (determined by measurement of OD260 nm):

|  | average | range of fluctuations |
|---|---|---|
| 24h | 50 µg | 47 - 54 µg |
| 72h | 30 µg | 26 - 34 µg |

A. Enzymatic restriction of DNA

B. PCR-Amplification of the hugl-gene
top row: 150 ng DNA/ 50 µl Reaction
bottom row: 300 g DNA/ 50 µl Reaction

COMPOSITIONS FOR ISOLATING AND/OR STABILISING NUCLEIC ACIDS IN BIOLOGICAL MATERIAL

This application is a United States national filing under 35 U.S.C. §371 of international (PCT) application No. PCT/EP01/05888, filed May 22, 2001, designating the US, and claiming priority to German Application No. 100 31 236.5, filed Jun. 27, 2000.

The present invention relates to new compositions for the isolation and/or stabilisation of nucleic acids in materials of biological origin. The compositions contain as an essential ingredient a cationic compound of general formula $$Y^+R_1R_2R_3R_4X^-$$

wherein

Y may denote nitrogen or phosphorus $R_1$, $R_2$, $R_3$ and $R_4$ independently of one another may denote a branched or unbranched $C_1$-$C_{20}$-alkyl group and/or a $C_6$-$C_{20}$-aryl group as well as a $C_6$-$C_{26}$-aralkyl group and $X^-$ may represent an anion of an inorganic or organic, mono- or polybasic acid and at least one proton donor as additive.

Preferred compositions are those wherein the cationic compounds consist of an ammonium salt wherein $R_1$ denotes a higher alkyl group, preferably with 12, 14 or 16 carbon atoms, and $R_2$, $R_3$ and $R_4$ in each case denote a methyl group.

Also preferred are compositions wherein $R_1$ denotes an aralkyl group, preferably a benzyl group, $R_2$ denotes a higher alkyl group—preferably with 12, 14 or 16 carbon atoms—and $R_3$ and $R_4$ denote a methyl group.

Bromide, chloride, phosphate, sulphate, formate, acetate, propionate, oxalate or succinate are preferred as anions.

$C_1$-$C_6$-alkyl generally denotes a branched or unbranched hydrocarbon group with 1 to 6 carbon atoms(s) which may optionally be substituted by one or more halogen atom(s)—preferably fluorine—which may be identical to or different from one another. The following hydrocarbon groups are mentioned by way of example:

methyl, ethyl, propyl, 1-methylethyl (iso-propyl), butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methyl-propyl.

The term higher alkyl group denotes a branched or unbranched $C_7$-$C_{20}$-alkyl group which may optionally be substituted by one or more halogen atom(s)—preferably fluorine—which may be identical to or different from one another. The following hydrocarbon groups are mentioned by way of example:

branched or unbranched heptyl, octyl, nonyl, decyl, undecyl, dodecyl, tetradecyl, hexadecyl, dodecadecyl and eicosyl.

$C_3$-$C_6$-alkenyl generally denotes a branched or unbranched hydrocarbon group with 3 to 6 carbon atom(s), with one or possibly more double bonds which may optionally be substituted by one or more halogen atom(s)—preferably fluorine—which may be identical to or different from one another. The following hydrocarbon groups are mentioned by way of example:

2-propenyl (allyl), 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl.

$C_3$-$C_6$-alkynyl generally denotes a branched or unbranched hydrocarbon group with 3 to 6 carbon atom(s), with one or possibly more triple bonds which may optionally be substituted by one or more halogen atom(s)—preferably fluorine—which may be identical to or different from one another. The following hydrocarbon groups are mentioned by way of example:

2-propynyl (propargyl), 2-butynyl, 3-butynyl, 1-methyl-2-propynyl, 2-methyl-2-propynyl, 2-pentynyl, 3-pentynyl, 4-pentynyl, 1-methyl-2-butynyl, 2-methyl-2-butynyl, 3-methyl-2-butynyl, 1-methyl-3-butynyl, 2-methyl-3-butynyl, 3-methyl-3-butynyl, 1,1-dimethyl-2-propynyl, 1,2-dimethyl-2-propynyl, 1-ethyl-2-propynyl, 2-hexynyl, 3-hexynyl, 4-hexynyl, 5-hexynyl, 1-methyl-2-pentynyl, 2-methyl-2-pentynyl, 3-methyl-2-pentynyl, 4-methyl-2-pentynyl, 1-methyl-3-pentynyl, 2-methyl-3-pentynyl, 3-methyl-3-pentynyl, 4-methyl-3-pentynyl, 1-methyl-4-pentynyl, 3-methyl-4-pentynyl, 4-methyl-4-pentynyl, 1,1-dimethyl-2-butynyl, 1,1-dimethyl-2-butynyl, 1,1-dimethyl-3-butynyl, 1,2-dimethyl-2-butynyl, 1,2-dimethyl-3-butynyl, 1,3-dimethyl-2-butynyl, 1,3-dimethyl-3-butynyl, 2,2-dimethyl-3-butynyl, 2,3-dimethyl-2-butynyl, 2,3-dimethyl-3-butynyl, 1-ethyl-2-butynyl, 1-ethyl-3-butynyl, 2-ethyl-1-butynyl, 2-ethyl-2-butynyl, 2-ethyl-3-butynyl, 1,1,2-trimethyl-2-propynyl, 1-ethyl-1-methyl-2-propynyl and 1-ethyl-2-methyl-2-propynyl.

Aryl, unless otherwise defined, denotes an aromatic mono- or polynuclear group with 4 to 22 C-atoms which may optionally contain one or two heteroatoms. Examples include: phenyl, naphthyl, anthracyl or pyrole, furan, thiophene, pyridine, pyridazine, pyrimidine or pyrazine, and which may optionally be mono- or polysubstituted independently of one another by halogen (F, Cl, Br, I)—preferably fluorine—or by an alkyl group.

Aralkyl denotes a mono- or polynuclear aryl group as hereinbefore defined which is bound to the cationic partial structure via a $C_1$-$C_6$-alkylene, $C_3$-$C_6$-alkenylene or a $C_3$-$C_6$-alkynylene bridge, to which the definitions of the $C_1$-$C_6$-alkyl, $C_3$-$C_6$-alkenyl and $C_3$-$C_6$-alkynyl groups apply accordingly. For the purposes of the present invention the benzyl group is preferred.

Suitable counterions $X^-$ preferably include all anions of hydrohalic acids or anions of mono- or dibasic organic acids such as acetate or oxalate, malonate, succinate or citrate.

Suitable proton donors for the purposes of the present invention are primarily saturated aliphatic monocarboxylic acids, unsaturated alkenyl-carboxylic acids, saturated and/or unsaturated aliphatic $C_2$-$C_6$-dicarboxylic acids, aliphatic ketocarboxylic acids or ketodicarboxylic acids as well as amino acids in addition to inorganic acids or the salts thereof, on their own or in combination. All the abovementioned organic acids may be used in unsubstituted form or as substituted derivatives, while—unless otherwise stated—the unsubstituted derivatives or derivatives mono- or polysubstituted by hydroxyl groups are preferred.

Saturated aliphatic monocarboxylic acids for the purposes of the present invention preferably include, in addition to formic acid, $C_1$-$C_6$-alkyl-carboxylic acids, of which acetic acid, propionic acid, n-butyric acid, n-valeric acid, isovaleric acid, ethyl-methyl-acetic acid (2-methyl-butyric acid), 2,2-dimethylpropionic acid (pivalic acid), n-hexanoic acid, n-octanoic acid, n-decanoic acid and also n-dodecanoic acid (lauric acid) are preferred. In addition, the ketocarboxylic acids derived from the abovementioned acids may also be used.

Examples of unsaturated alkenyl-carboxylic acids for the purposes of the invention include for example acrylic acid (propenoic acid), methacrylic acid, crotonic acid, isocrotonic acid as well as vinylacetic acid.

According to the present invention, saturated aliphatic $C_2$-$C_6$-dicarboxylic acids, such as for example oxalic acid, malonic acid, succinic acid, glutaric acid or adipic acid are preferred, while oxalic acid and succinic acid are particularly preferred.

It is particularly preferable, in order to solve the problem according to the invention, to use aliphatic hydroxy-di- and -tricarboxylic acids, of which tartronic acid, D-(+), L-(−) or DL-malic acid, (2R, 3R)-(+)-tartaric acid, (2S, 3S)-(−)-tartaric acid, meso-tartaric acid and citric acid are most particularly preferred.

Unsaturated dicarboxylic acids such as maleic or fumaric acid or unsaturated tricarboxylic acids, such as for example aconitic acid, are also suitable as solutions to the problem of the present inventions.

For the purpose of the present invention, however, aliphatic ketodicarboxylic acids may also be used as additives, such as e.g. mesoxalic acid and oxaloacetic acid, of which oxaloacetic acid is most particularly preferred.

Moreover, according to the present invention, amino acids may be used, of which α-amino acids—such as e.g. aminoacetic acid (glycine), α-aminopropionic acid (alanine), α-amino-iso-valeric acid (valine), α-amino-iso-caproic acid (leucine) and α-amino-β-methylvaleric acid (isoleucine) are preferred. Glycine is most preferably used.

The proton donors mentioned above may be used as individual substances or in the form of the pure stereoisomers and also in mixtures.

As further additives, mineral acids and their salts may also be used according to the present invention. Preferably, the salts of mineral acids—such as phosphoric acid or sulphuric acid—with alkali metals or the ammonium salts thereof are used. Phosphoric acid and ammonium sulphate are most preferably used.

The term nucleic acids for the purposes of the present invention denotes nucleic acids in the wider sense, and thus includes, for example, ribonucleic acids (RNA) and also deoxyribonucleic acids (DNA) in all lengths and configurations, such as double-stranded, single-stranded, circular and linear, branched, etc., and all possible subunits thereof, such as e.g. monomeric nucleotides, oligomers, plasmids, viral and bacterial DNA and RNA, as well as genomic and non-genomic DNA and RNA from animal and plant cells or other eukaryotes, mRNA in processed and unprocessed form, tRNA, hn-RNA, rRNA, cDNA as well as all other conceivable nucleic acids.

The biological sample with nucleic acids used may be cell-free sample material, plasma, body fluids such as blood, serum, cells, leucocyte fractions, crusta phlogistica, sputum, urine, sperm, faeces, smears, aspirates, tissue samples of all kinds, such as biopsies, for example, parts of tissues and organs, food samples which contain free or bound nucleic acids or cells containing nucleic acids as envisaged according to the invention, such as for example organisms (single- or multi-cell organisms; insects, etc), plants and parts of plants, bacteria, viruses, yeasts and other fungi, other eukaryotes and prokaryotes, etc., as disclosed for example in European Patent Application No. 95909684.3, to which reference is hereby made, or free nucleic acids.

Regarding the technological background to the invention:

It is sufficiently well known from the prior art that the genetic origin and functional activity of a cell can be determined and investigated by studying its nucleic acids. The analyses of the nucleic acids and proteins provide direct access to the cause of cell activities. They are thus potentially superior to indirect conventional methods such as, for example, the detection of metabolic products. Thus, molecular biological analyses are already used in many fields, e.g. in medical and clinical diagnostics, in the pharmaceutical field in the development and evaluation of pharmaceutical compositions, in food analysis and also in monitoring food production, in agriculture in the cultivation of crops and farm animals as well as in environmental analysis and numerous fields of research.

By analysing the RNA, particularly the mRNA in cells, it is possible to determine the activities of genes directly. The quantitative analysis of transcription patterns (mRNA patterns) in cells by modem methods of molecular biology, such as e.g. Real time Reverse Transcriptase PCR or gene expression chip analyses makes it possible for example to detect wrongly expressed genes, thereby detecting metabolic disorders, infections or the development of cancer. The analysis of the DNA from cells by molecular biological methods such as e.g. PCR, RFLP, AFLP, SNP or sequencing makes it possible for example to detect genetic defects or to determine the HLA type and other genetic markers.

The analysis of genomic DNA and RNA is also used for directly detecting infectious pathogens such as viruses, bacteria etc.

It is an absolute prerequisite for nucleic acid analysis to stabilise the nucleic acids and proteins immediately after the biological sample has been taken from its natural environment. This applies to DNA and particularly RNA, which can be broken down very rapidly after the biological sample has been taken. On the other hand, once the biological sample has been taken, new mRNA molecules may be synthesized by the induction of stress genes, for example, thereby changing the transcription pattern of the cells. This can falsify subsequent analysis. In the medical field in particular it is essential to stabilise nucleic acids as it is common in practice for samples containing nucleic acids to be taken and then not investigated further until they have first been stored for some time and transported to a laboratory.

In the meantime, the nucleic acids contained in the samples can change or even break down completely. This naturally has a massive influence on the results of any tests carried out subsequently or makes them completely impossible. Such tests are carried out using molecular biological techniques such as, for example, Northern and Southern Blot Analysis, PCR, RT-PCR, SunRise, LCR, branched DNA (bDNA), SDA, DNA and RNA chips and arrays for gene expression and mutation analysis, RFLP, AFLP, SNP Analysis, cDNA Synthesis, subtractive hybridisation or Taqman technology and other real time quantifying methods. On the other hand, the use of highly purified intact nucleic acid-DNA or RNA-constitutes a criterion of fundamental relevance for the use or carrying out of the above mentioned tests. In addition, the isolation of the samples containing nucleic acid and the assays also constitutes a time consuming operation. Moreover, contamination of an investigating laboratory working in the field of molecular biology-such as may occur for example if a test goes wrong—may lead to erroneous test results.

Regarding the Prior Art

A large number of publications propose the use of mixtures based on ethanol and acetone as fixatives for the subsequent isolation of nucleic acid from a suitable sample such as tissue, for example. After studying this literature it is clear that ethanol/acetone mixtures of this kind by no means satisfy all the requirements imposed on safe recovery of RNA. Thus, mixtures of this kind are incapable of protecting the RNA from breakdown. In addition, there is no guaranteed protection of the RNA in solid samples made up of more extensive cell aggregates. Moreover, the proposed mixtures are highly inflammable or explosive, which adds substantially to the risks when working in the laboratory.

In addition, a more peripherally relevant prior art is concerned with the recovery of RNA from fixed or preserved tissue samples. This relates particularly to the suitability of histological preparations for maximising the signal strength achieved during in situ hybridisation. In other words, experiments of this kind are intended to detect RNA rather than preserve it (U.S. Pat. Nos. 5,196,182 and 5,260,048).

Other reports relate to the recovery of fragmented RNA or DNA from a fixed tissue in order to be able to subject the fragments thus obtained to restricted molecular analysis by PCR. In order to obtain fragmented DNA or RNA of this kind the corresponding samples are conventionally treated with Proteinase K in order to be able to break down the structural tissue components; only then is the RNA extracted with a solution which contains guanidinium salt. The RNA obtained from fixed tissue by this method is, however, of poor quality and is only about 200 bases in size. According to the prior art this can be put down to a certain number of particular factors which include, inter alia, the negative effects of endogenous and crosslinking reactions of the DNA or RNA within the intracellular matrix during fixing. Based on the fact that the DNA or RNA is at least partially degraded in the majority of cases, DNA or RNA obtained in this way can no longer be used successfully in Northern analysis. RNA isolated in this way could at most be used with some prospects of success in an RT-PCR reaction, but only to amplify relatively small fragments.

The prior art also describes the use of ammonium sulphate for preserving RNA at temperatures above freezing [WO 00/06780]. A composition of this kind has been used according to the prior art under the name RNAlater. However, aqueous ammonium sulphate solutions of this kind are not suitable for stabilising RNA in blood, plasma or sera. Because the samples mentioned have a high protein concentration, a precipitate of limited solubility is immediately formed on contact with ammonium salt solutions of this kind [RNAlater product information from Messrs Ambion, Austin, Tex., USA].

Moreover, it has long been known from the prior art to use cationic compounds of this kind to isolate nucleic acids from biological samples. Such applications are described for example in U.S. Pat. Nos. 5,010,183 and 5,300,635 and in European Patent EP 0442026. In these publications, the biological sample is incubated with the cationic compound for the incubation periods which are conventional for sample preparation, i.e. of the order of some minutes; then the nucleic acid is purified again.

A study of the compounds known from the prior art has shown that the cationic compounds mentioned in the prior art, particularly tetradecyltrimethyl ammonium oxalate which is disclosed in the US patents, do not on their own guarantee adequate stabilisation of cellular RNA, e.g. when blood is stored for long periods.

Admittedly, experiments are known from the prior art which set out, for example, to stabilise viruses in blood for a period of several days, but these findings contain no references whatever to the RNA remaining intact. Thus, Schmidt and MacFarlane [J. Medical Virology 47, (1995) 153] describe the stabilisation of Hepatitis C virus in blood by means of Catrimox-14™ for seven days at ambient temperature. The viruses were detected by RT-PCR amplification of a 250 bp long fragment of the HCV genome. The results disclosed did not, however, provide sufficient evidence of the intactness of the RNA as only a small fragment was amplified. Moreover, the experiment was carried out with a sample of indeterminate virus loading, so that it was impossible to make any pronouncements as to the breakdown of viral RNA during storage.

In addition, International Patent Application WO 99/29904 describes the stabilisation of DNA in body fluids using EDTA, EGTA or BAPTA in conjunction with guanidine hydrochloride, guanidine thiocyanate, lithium chloride, manganese chloride, sarcosyl, SDS, sodium perchlorate, sodium salicylate and sodium thiocyanate. Moreover, it is known from the prior art that reagents which contain phenol, such as Trizol™, for example, can be used to stabilise RNA during storage. However, all these reagents are very harmful to health and are therefore not suitable for routine use.

The aim of the present invention is therefore to provide a composition which stabilises RNA in the presence of tissue or blood, plasma or serum.

The invention additionally sets out to provide a composition in the form of a stabilising solution the ingredients of which are not harmful to health and may thus also be used, for example, to stabilise biological sample material while it is being transported from the place where the sample is obtained to a laboratory without any health risks to the staff handling the sample.

A further objective of the present invention is to provide a composition in the form of a stabilising solution which meets the requirement that the stabilising reagent should itself also remain stable in solution and requires no pre-treatment—such as for example the dissolving of precipitates of limited solubility—by the user. Pre-treatments of this kind always involve a risk of variations in the stabilising efficiency.

A further objective of the present invention is to provide a composition which is versatile in use, i.e. which can be used for a wide spectrum of biological samples.

Surprisingly it has now been found that nucleic acids can be stabilised over a long time if the nucleic acids of a biological sample are brought into contact with a cationic compound such as those disclosed inter alia in U.S. Pat. Nos. 5,010,183 and 5,300,645 and combined according to the invention with one or more of the additives described above. Preferred additives which are suitable for solving the problem according to the invention are listed in Table 1:

TABLE 1

| Name | Formula |
| --- | --- |
| acetic acid | $CH_3$—COOH |
| oxalic acid | HOOC—COOH |
| malonic acid | HOOC—$CH_2$—COOH |
| tartronic acid | HOOC—CHOH—COOH |
| succinic acid | HOOC—$CH_2$—$CH_2$—COOH |
| malic acid | HOOC—CHOH—$CH_2$—COOH |
| tartaric acid | HOOC—CHOH—CHOH—COOH |
| glutaric acid | HOOC—$CH_2$—$CH_2$—$CH_2$—COOH |
| adipic acid | HOOC—$CH_2$—$CH_2$—$CH_2$—$CH_2$—COOH |
| citric acid | HOOC—$CH_2$—COHCOOH—$CH_2$—COOH |
| maleic acid | HOOC—CH=CH—COOH |
| oxaloacetic acid | HOOC—CO—$CH_2$—COOH |
| glycine | $H_2N$—$CH_2$—COOH |
| ammonium sulphate | $(NH_4)_2SO_4$ |
| phosphate | $H_3PO_4$ K and Na salt |

The additive may be present in the stabilising reagent in various concentrations; for example, it may be present in mixtures of the stabilising solution with blood in a ratio by volume of 1:1—preferably 3:1 in a concentration from 50 mM to saturation, preferably from 100 to 1 M and most preferably in a concentration of 200-500 mM. Depending on the nature of the additive, other concentration ranges may prove advantageous. It is also possible to use combinations of different additives.

The concentration of the cationic compound in the aqueous solution of the composition is in the range between 0.01% by weight and saturation, preferably between 0.1% and saturation, more preferably between 0.5 and 15% by weight and most preferably between 2 and 10% by weight.

Naturally, when adding a solution of cationic compounds and additive, the optimum concentrations are determined by the respective volume of the biological sample and the ratio by volume of the stabilising solution to the biological sample.

The pH of the mixture of cationic compound and additive may in general be varied as a function of the sample over a wide pH range (pH 2 to 12) and is preferably in a range from pH 2 to pH 10 and more preferably in a range from pH 3 to 8. The preferred pH range is dependent on the biological sample used. For blood, plasma and serum a pH value in a range between pH 2 and pH 6 and especially between pH 3 and pH 4 is preferred.

For biological samples such as other cellular body fluids apart from blood, plasma and serum, or e.g. bacteria, aspirates, cells, tissues and other biological samples—such as those described above—the pH value in the stabilising solution consisting of cationic compound and additive is preferably in the range from pH 3 to pH 10 and more preferably in a range from pH 4 to pH 8.

To stabilise nucleic acids in biological samples, the sample may be mixed with a solution which contains the cationic compound(s) and additives. It is possible to add 0.1 to 10,000 volumes of the biological sample; preferably a volume ranging from 1 to 1000 is added, most preferably a volume in the range from 1 to 100. Depending on the nature of the sample, however, such as for example samples from fine needle biopsies or low cell count cultures, substantially higher volumes may also be used in some cases.

Similarly, the abovementioned cationic compounds and additives may also be added in solid form if the biological sample itself contains liquid to dissolve the solid (such as for example cell-containing body fluids, cells in medium, urine) or if liquid, e.g. water is added thereto to dissolve the solid.

The advantage of adding a solid is that solids are usually chemically more stable and they are often easier to add to the sample.

Moreover, particularly with very compact biological samples such as tissues, for example, it is possible to grind up or homogenise the sample in the stabilising solution or before mixing it with the stabilising solution, in order to assist the release of nucleic acids or individual cells or cell aggregates, by destroying a compact sample by, for example, mechanical, chemical, physical or enzymatic action on the sample. Mechanical action may be carried out with an electric knife, a bead mill or by squeezing through a syringe, for example, while suitable enzymes for acting on the sample might be, for example, hydrolases, proteases or lipases.

In addition, the sample may be pre-treated by purely physical means, e.g. with ultrasound.

The pre-treatment may also be carried out chemically, either alone or in conjunction with purely physical methods. Means of assisting lysis include, for example, the use of aliphatic alcohols—particularly isopropanol—or aldehydes or dialdehydes—such as e.g. glyoxal—or also phenols or phenol derivatives—such as e.g. 2-biphenylol or ionic, zwitterionic and non-ionic compounds,—such as e.g. mercapto—or reducing reagents—such as e.g. dithiothreitol and β-mercaptoethanol—or phosphoric acid derivatives—such as e.g. tributylphosphate—or chaotropic reagents, such as e.g. urea, guanidinium thiocyanate or guanidinium hydrochloride—or salts, either individually or in combination.

Other possible ways of mechanically, chemically, physically or enzymatically acting on samples are known in the art and are intended to be included here.

The sample material may be stored for fairly long periods, depending on the particular requirements, such as e.g. from 1 to 14 days or longer, at ambient temperature, but also at elevated temperatures, such as e.g. 40° C. or more, and also at lower temperatures such as e.g. 4° C. or –20° C. or below.

The storage of the biological sample in the solution of the abovementioned compounds may either be followed directly by techniques for analysing nucleic acids, or the nucleic acids may be purified from the sample.

Nucleic acids may be directly detected/analysed, for example, by blotting methods, gel-electrophoresis methods for separating biomolecules and chromatographic methods.

In order to purify the nucleic acids from the biological sample the free nucleic acids or cells or particles containing nucleic acids are separated from the rest of the solution by centrifuging or filtering, for example, and subjected to further purification which may advantageously take place in a small volume, as described in U.S. Pat. Nos. 5,010,183, 5,300,645 and in European Patent Application No. 99103457.0.

Directly separating the nucleic acids or the cells or particles containing nucleic acids in the storage vessel does away with additional steps for transferring the sample into other containers for purification and thus reduces the losses of sample and also minimises the risk of mix-ups and contamination by nucleic acids being picked up from sample to another. The use of these stabilising reagents thus leads to a one step process for stabilising and directly isolating nucleic acids in biological samples, in which RNA and DNA can be alternatively isolated from the biological sample or isolated in parallel from one sample.

By stabilising nucleic acids using the composition according to the invention comprising one or more cationic compounds and one or more additives, it is ensured that the nucleic acids in a sample will not change even during lengthy storage periods or while being transported. Thus, the accuracy of any subsequent tests is significantly enhanced. In certain cases, for example if the sample material has to be transported for long distances or stored for longer periods, the process according to the invention makes it possible for the first time for these tests to be carried out after such a period of time.

The advantages of this invention are found particularly in the field of research, e.g. for analysing transcript levels which have to be fixed directly after sampling, and in the field of clinical analysis, such as molecular diagnostics, for example, in which patient samples also have to be stabilised during storage and transportation until they are ready to be analysed. In particular, the isolation and stabilisation of nucleic acids is used in tumour diagnosis, in the diagnosis of inherited diseases as well as in the diagnosis and monitoring of viruses and the diagnosis and monitoring of other infectious agents and in the analysis of gene expression patterns.

The field of application of the present invention extends not only to medical or zoological fields but also includes the analysis of botanical, fungal and prokaryotic systems. The stabilisation and isolation of nucleic acids from plants and parts of plants, algae, fungi and bacteria from cultures and natural habitats are used in research, e.g. for analysing transcript levels and gene expression patterns and for identifying and quantifying species in complex populations, such as bacteria in a soil sample.

The potential applications also include other analytical fields such as food analysis, for example.

The present invention will be illustrated by the following examples and the figures. In the description and examples the following abbreviations are used:

| | |
|---|---|
| AFLP | amplified fragment length polymorphism |
| A. dest. | distilled water |
| BAPTA | 1,2-bis(2-aminophenoxy)ethane-N,N,N',N'-tetraacetic acid |
| EcoRI | restriction enzyme *Escherichia coli* strain R |
| $E_{260}/E_{280}$ | quotient of extinctions at 260 and 280 nm |
| EDTA | ethylenediamine-N,N,N',N'-tetraacetic acid |
| EGTA | [ethylenebis(oxyethylenenitrilo)] tetraacetic acid |
| GAPDH | glycerine aldehyde-3-phosphate-dehydrogenase |
| Hind III | restriction enzyme *Haemophilus influenzae* |
| hugl | human homologue of giant larvae |
| IFN-γ | interferon-gamma |
| LM | length marker |
| MOPS | 3-(N-morpholino)-2-hydroxypropanesulphonic acid |
| nb | not determined |
| Nonidet P40 | imbentin-N/52; octylphenylpolyethyleneglycol |
| OD | optical density |
| PBS | phosphate buffered saline |
| PCR | Polymerase Chain Reaction |
| RFLP | restriction fragment length polymorphism |
| rpm | revolutions per minute |
| mRNA | messenger RNA |
| rRNA | ribosomal RNA |
| RT | room temperature |
| RT-PCR | Reverse Transcriptase PCR |
| SDS | sodium dodecylsulphate |
| SNP | Single Nucleotide Polymorphism |
| SSC | common salt/sodium citrate solution |
| TBE | Tris-Borate-EDTA buffer |
| Tris | 2-amino-2-(hydroxymethyl)-1,3-propanediol |
| U | units |

Abbreviations not listed here, such as e.g. h for hour(s), will be familiar to anyone skilled in the art or will be sufficiently well known from their use in the prior art.

EXPLANATIONS OF THE FIGURES AND THE EXPERIMENTS ON WHICH THEY ARE BASED

Figure 5:
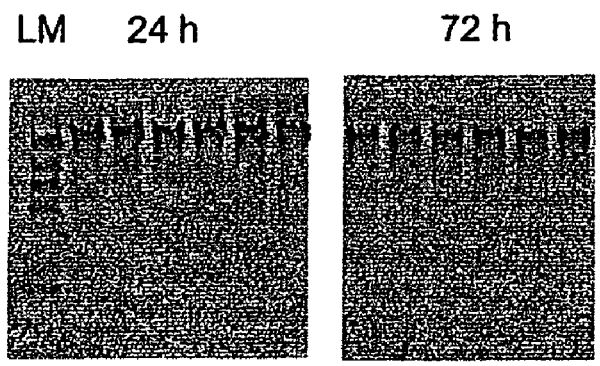
FIG. 5 shows the stabilisation of genomic DNA in blood by means of tetradecyltrimethyl ammonium oxalate buffered with tartaric acid at pH 3.7.

In addition to cellular RNA, genomic DNA from the white blood corpuscles can also be stabilised by the method developed here and then isolated by binding to a silica membrane. FIG. 5 shows that even after 72 hours' storage high-molecular DNA (length>20 kB) is isolated.

Figure 6:
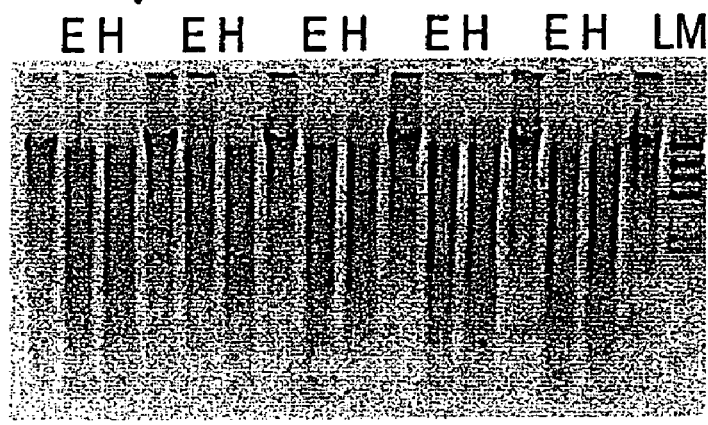
Figure 6:
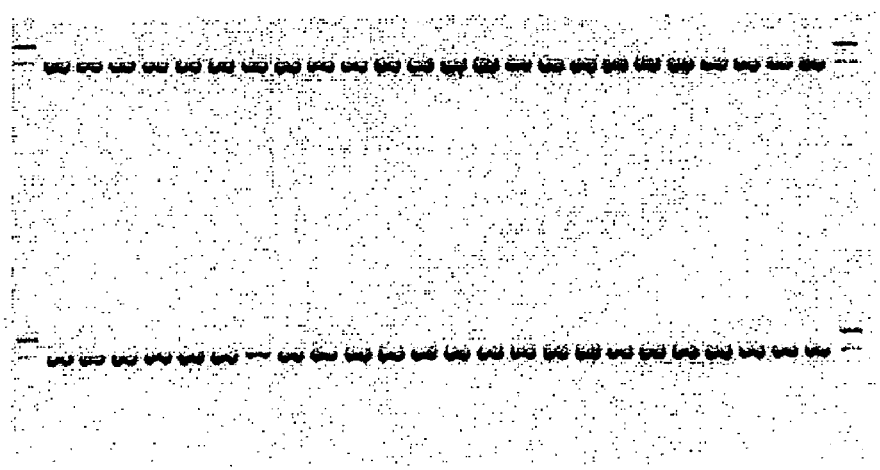

FIG. 6 shows the results when genomic DNA is used in enzymatic reactions. The DNA isolated after storage for 24 or 72 hours (cf Example 5) is used in various enzymatic reactions.

A. 2 µg of the DNA are cut with 6 U of the restriction enzymes EcoRI (E) or Hind III (H) for 3 h at 37° C. and then separated on a 0.8% agarose/TBE gel. As a control in each case the uncut DNA is applied.

B. 150 and 300 ng aliquots of the genomic DNA are used in a PCR reaction (total volume 50 µl), in which a 1.1 kB long fragment of the hugl gene (human homologue of giant larvae) is amplified. The PCR products are separated on a 1.2% agarose/TBE gel.

Figure 7:
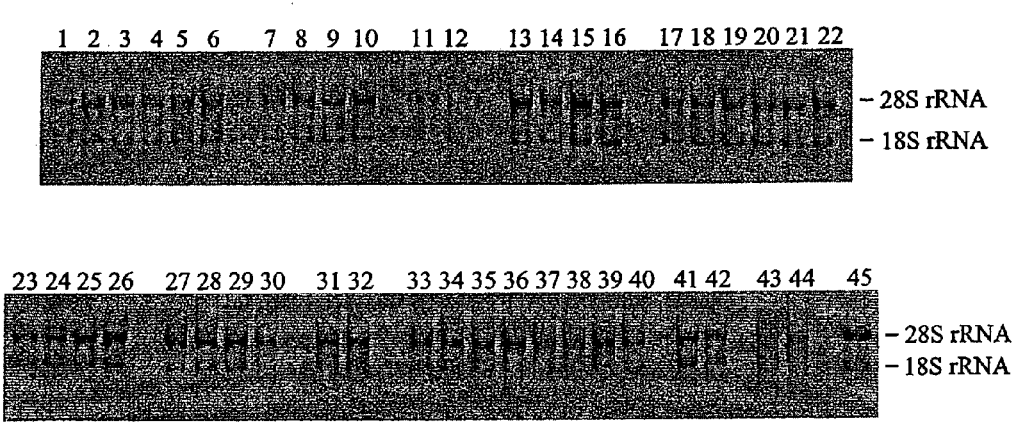

FIG. 7 shows the stabilisation of RNA in plasma by means of tetradecyltrimethyl ammonium oxalate mixed with various additives. All the samples are prepared as double measurements: 30 µl aliquots of the eluates are separated in a 1% agarose-formaldehyde-MOPS gel. The samples in question are listed in Table 2.

Figure 8:
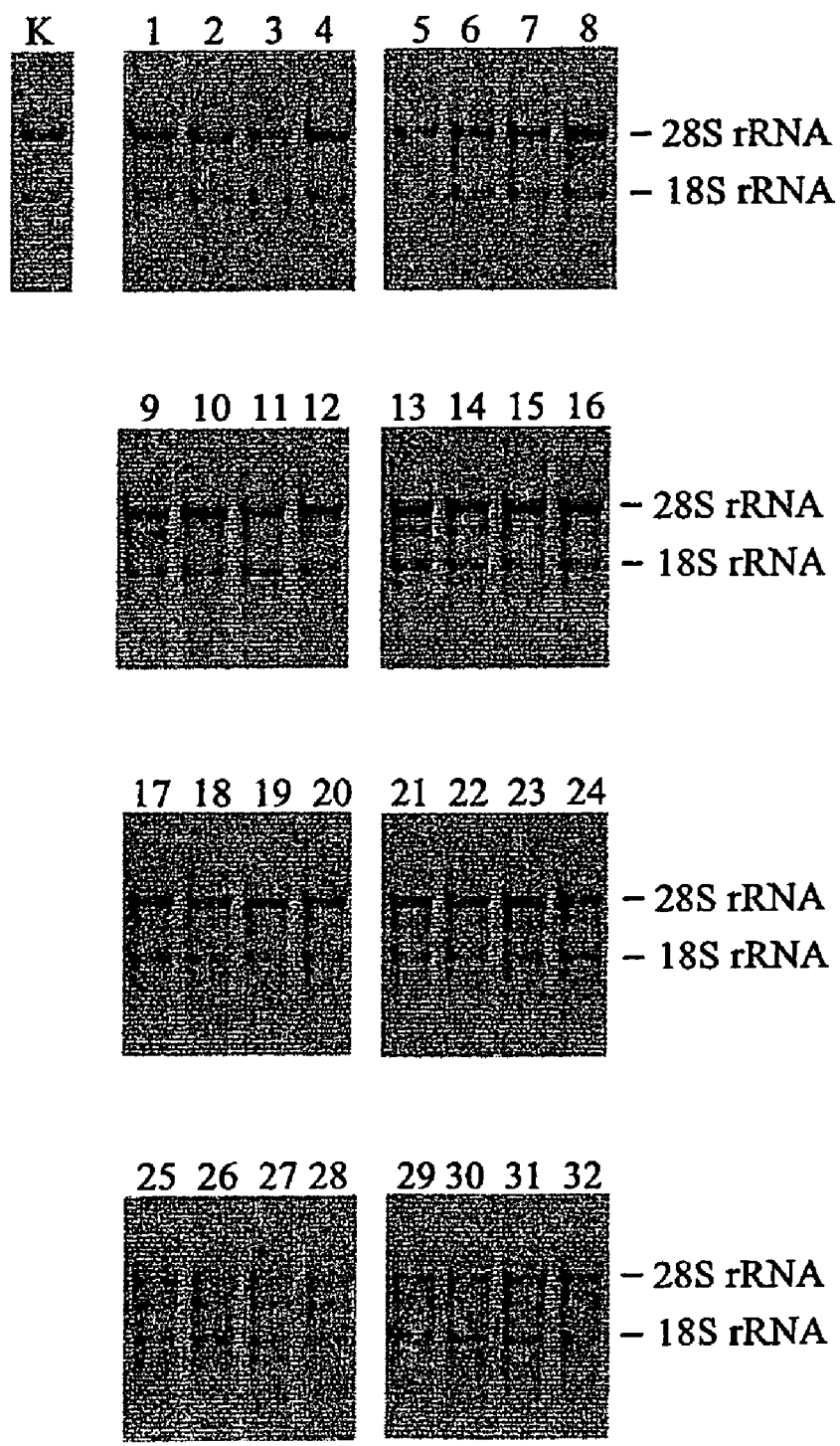

FIG. 8 shows the stabilisation of RNA in plasma by means of tetradecyltrimethyl ammonium oxalate mixed with tartaric or tartronic acid over various periods of time.

All the samples are prepared as double measurements: 30 µl aliquots of the eluates are separated in a 1% agarose-formaldehyde-MOPS gel. The samples in question are listed in Table 3.

Figure 9:
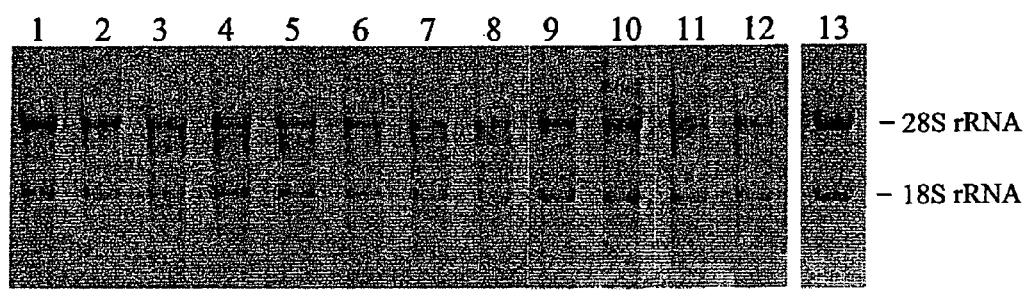

FIG. 9 shows the stabilisation of RNA in 1 ml plasma by means of tetradecyltrimethyl ammonium oxalate mixed with various additives.

All the samples are prepared as double measurements: 30 µl aliquots of the eluates are separated in a 1% agarose-formaldehyde-MOPS gel. The samples in question are listed in Table 4.

Figure 10:
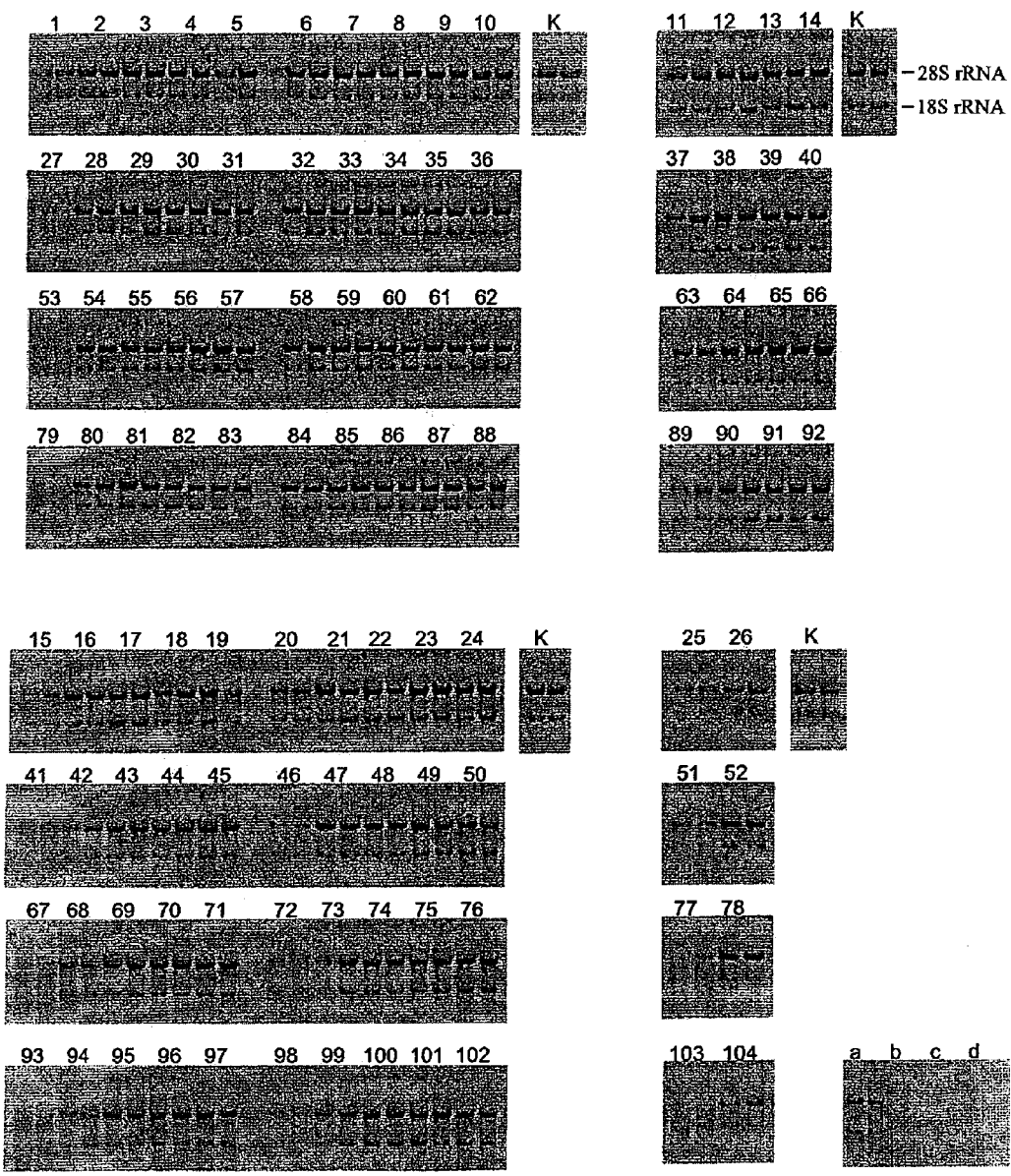

FIG. 10 shows the stabilisation of RNA in HeLa cells by means of tetradecyltrimethyl ammonium oxalate mixed with various additives.

The samples are prepared as double measurements, samples 14, 40, 66 and 92 as single measurements: 20 µl aliquots of the eluates are separated in a 1% agarose-formaldehyde-MOPS gel. The samples in question are listed in Table 5.

Figure 11:
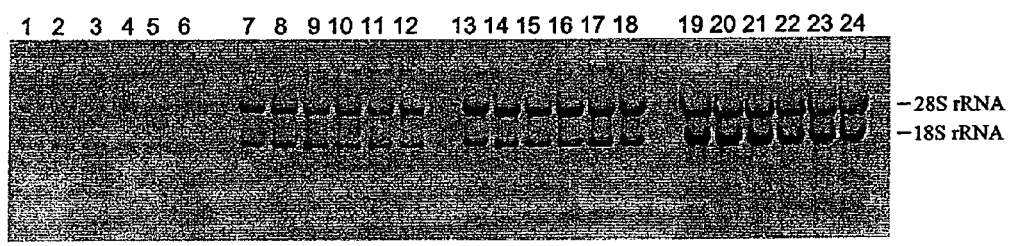

FIG. 11 shows the stabilisation of RNA in different amounts of HeLa cells. All the samples are prepared as double measurements: 20 µl aliquots of the eluates are separated in a 1% agarose-formaldehyde-MOPS gel. The samples in question are listed in Table 7.

Figure 12:
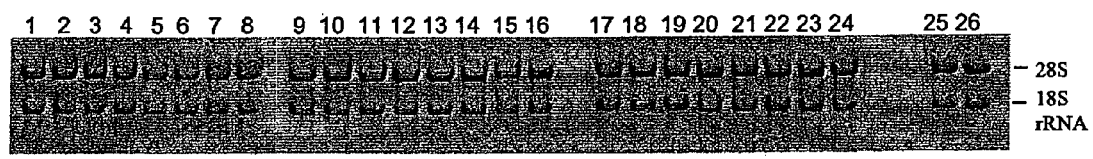

FIG. 12 shows the stabilisation of RNA in macrophages. All the samples are prepared as double measurements: 20 µl aliquots of the eluates are separated in a 1% agarose-formaldehyde-MOPS gel. The samples in question are listed in Table 9.

Figure 13:
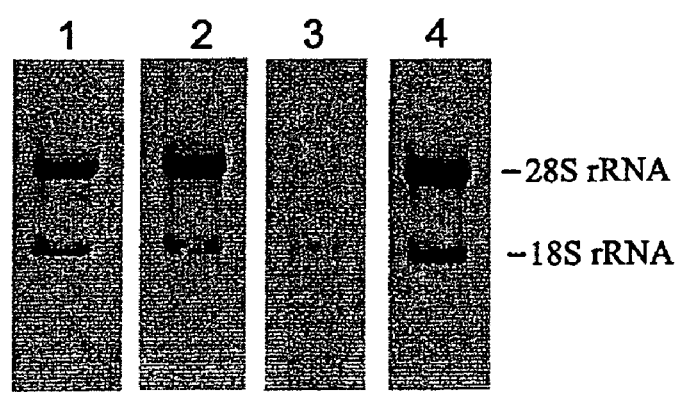

FIG. 13 shows the stabilisation of RNA in adherent Hela cells without removing the medium. 20 µl aliquots of the eluates are separated in a 1% agarose-formaldehyde-MOPS gel. The samples in question are described in Example 13.

Figure 14:
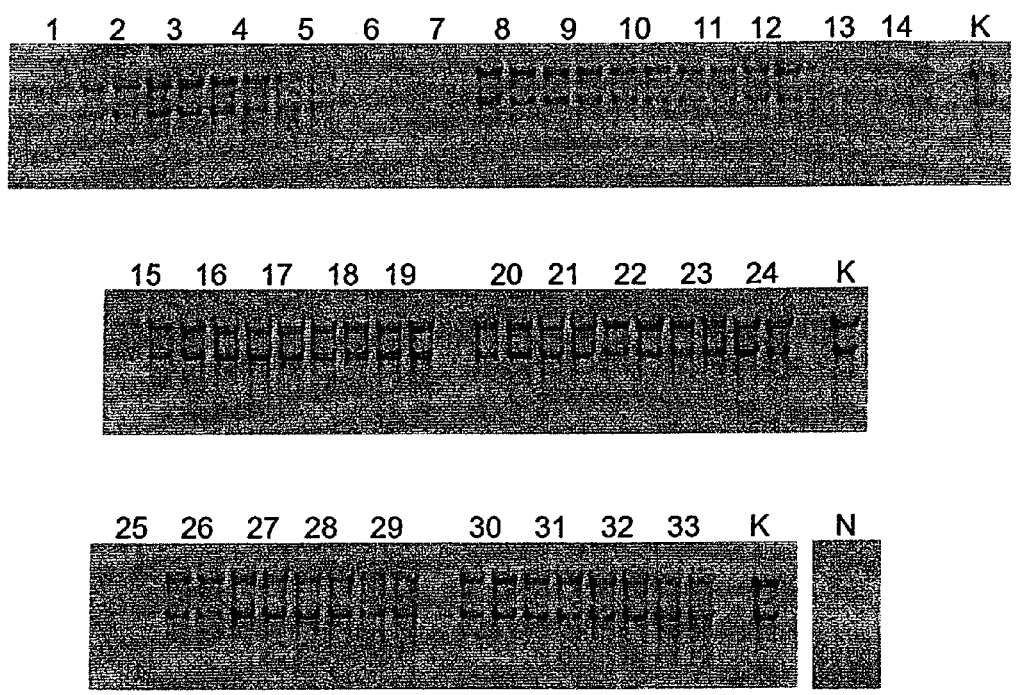

FIG. 14 shows the stabilisation of RNA in kidney tissue by means of tetradecyltrimethyl ammonium oxalate mixed with various additives.

All the samples are prepared as double measurements: 20 µl aliquots of the eluates are separated in a 1% agarose-formaldehyde-MOPS gel. The samples in question are listed in Table 12.

Figure 15:
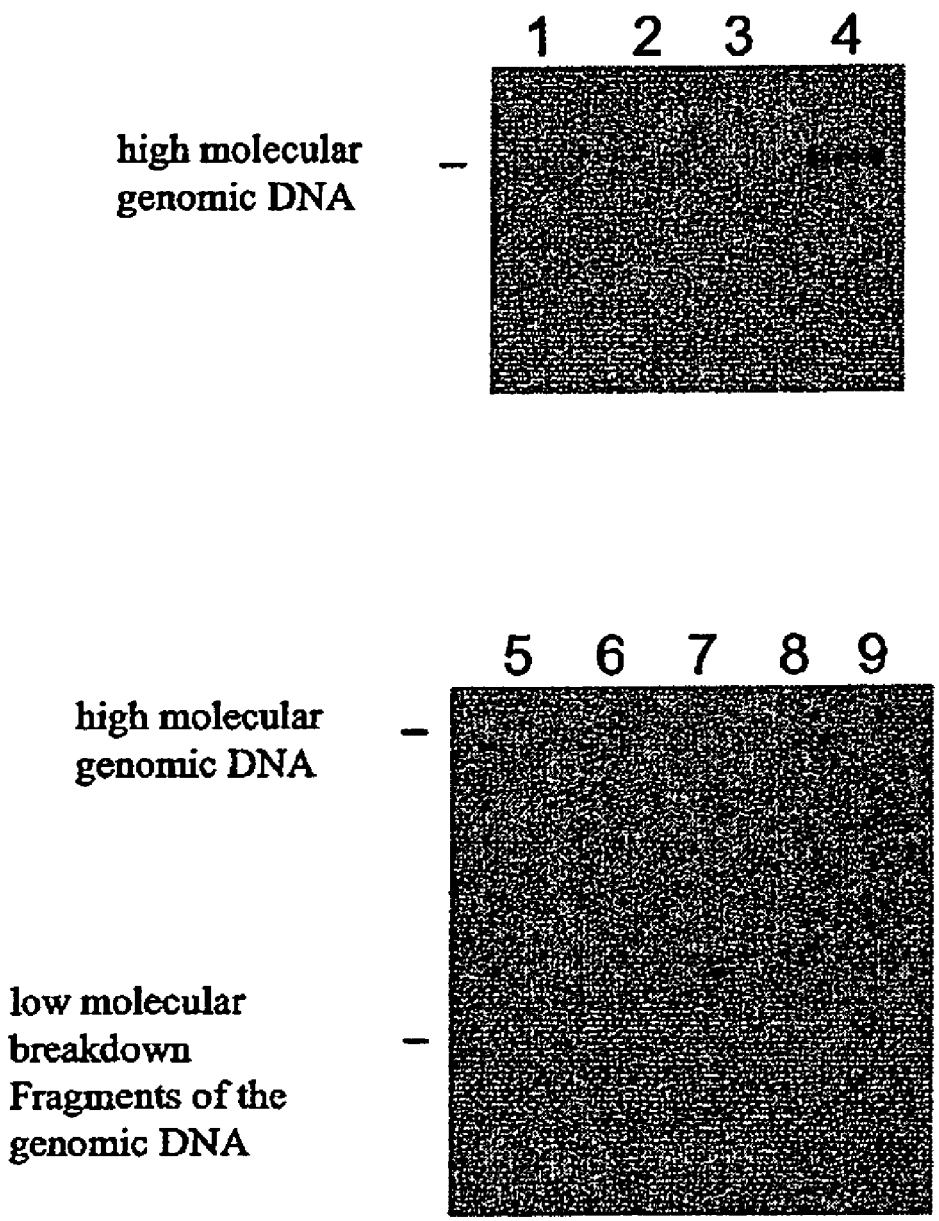

FIG. 15 shows the stabilisation and isolation of DNA parallel to the stabilisation and isolation of RNA. 40 µl aliquots of the eluates are separated in a 0.8% agarose-TBE gel. The samples in question are described in Example 15.

EXAMPLES

Example 1

Stabilisation of RNA in Blood by Means of Tetradecyltrimethyl Ammonium Oxalate (TTAOx) in Various Carboxylic Acid Buffers at Different pH Levels Carboxylic acids of various chain lengths are used as additives. In addition, mono-, di- and tricarboxylic acids, hydroxylated and non-hydroxylated carboxylic acids are tested. All the substances are used for stabilisation in conjunction with the cationic compound tetradecyltrimethyl ammonium oxalate. Both the pH and the concentration of the substances is varied.

Figure 1:
FIG. 1 shows the stabilisation of the RNA in blood by means of tetradecyltrimethyl ammonium oxalate (TTAOx) in various carboxylic acid buffers with different pH levels
Figure 1:
Figure 1:
Figure 1:
Figure 1:
Figure 1:
Figure 1:
Figure 1:
Figure 1:
Figure 1:

FIG. 1 shows the results of the tests. In every case, intact RNA can be isolated even after 24 and 48 hours. The quantities of RNA, which are small in some cases, correspond to the low volume of blood being processed and the differing RNA content in various blood samples. In this experiment some of the genomic DNA was also obtained in the RNA fractions.

500: 1 of blood are stored for 24 and 48 hours at RT with 500: 1 of a buffer consisting of 10% (w/v) tetradecyltrimethyl ammonium oxalate buffered with various carboxylic acids, each in a concentration of 200 mM, and at the various pH levels for the carboxylic acid in question. In order to isolate the RNA the complexes consisting of cationic compound and nucleic acid are centrifuged; the pellet is washed once with water, centrifuged again and taken up in 300: 1 of a standard commercial lysing buffer such as, for example, RLT buffer made by QIAGEN. The sample is diluted with 360: 1 of water and treated for 10 minutes at 55° C. with 40: 1 of Proteinase K. Then the sample is centrifuged, ethanol is added to the supernatant and it is added to a spin column containing a silica membrane. The sample is passed through the membrane by centrifuging. The spin column is washed once with a commercially obtainable guanidinium isothiocyanate-containing washing buffer, e.g. the buffer RW1 made by QIAGEN, and twice with a standard commercial alcohol-containing washing buffer such as the buffer RPE made by QIAGEN, and the RNA is then eluted in 60: 1 of RNase-free water which is also passed through the membrane by centrifuging. 30: 1 aliquots of the eluate are separated on a 1.2% agarose/formaldehyde gel.

Example 2

Stabilisation of RNA in Whole Blood Using Tetradecyltrimethyl Ammonium Oxalate and Tartaric Acid (Buffered) at pH 3 in Various Concentrations.

500: 1 of blood are stored for 2.5, 24 and 48 hours at RT with 500: 1 of a buffer consisting of 10% (w/v) tetradecyltrimethyl ammonium oxalate and 50-500 mM tartaric acid, pH 3. The RNA is isolated as described in FIG. 1 except that in addition the genomic DNA is eliminated by DNase treatment of the sample with the "RNase-free DNase set" made by QIAGEN. The RNA is eluted with 80: 1 of RNase-free water. 30: 1 of the eluate are separated on a 1.2% agarose/formaldehyde gel.

Example 3

Stabilisation of RNA in Whole Blood Using Tetradecyltrimethyl Ammonium Oxalate Buffered with 250 mM Tartaric Acid at pH 3.

Figure 3:
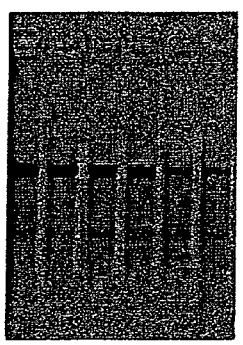
FIG. 3 shows the stabilisation of the RNA in whole blood by means of tetradecyltrimethyl ammonium oxalate buffered with 250 mM tartaric acid, pH 3.

Determining the integrity, yield and purity of the RNA:

The RNA is stabilised in blood for at least 72 hours without any degradation or loss of yield in a solution of tetradecyltrimethyl ammonium oxalate buffered with a carboxylic acid buffer, e.g. 250 mM tartaric acid, pH 3.0 (see FIG. 3).

2 ml of blood are mixed with 2 ml of a buffer consisting of 10% (w/v) tetradecyltrimethyl ammonium oxalate and 250 mM tartaric acid pH 3.0 and stored for 24-72 hours at RT. The RNA is isolated as described in Example 2 except that a standard commercial erythrocyte lysing buffer—such as e.g. the buffer EL made by Qiagen GmbH—is added to the sample before the centrifugation of the complexes—consisting of the cationic compound and the nucleic acid—and the mixture is then incubated on ice for 10 minutes. The RNA is eluted with 80 µl of RNase-free water. 30 µl aliquots of the eluate are separated on a 1.2% agarose/formaldehyde gel, or measured in a spectral photometer. The amount of isolated total RNA is determined after dilution with water by photometric measurement of the light absorption at a wavelength of 260 nm. The purity of the RNA thus obtained is measured by photometrically determining the ratio of light absorption at 260 nm to that at 280 nm.

Example 4

Stabilisation of the RNA in Whole Blood by Means of Different Concentrations of Tetradecyltrimethyl Ammonium Oxalate, Buffered with Tartaric Acid at pH 4.0

Figure 2:
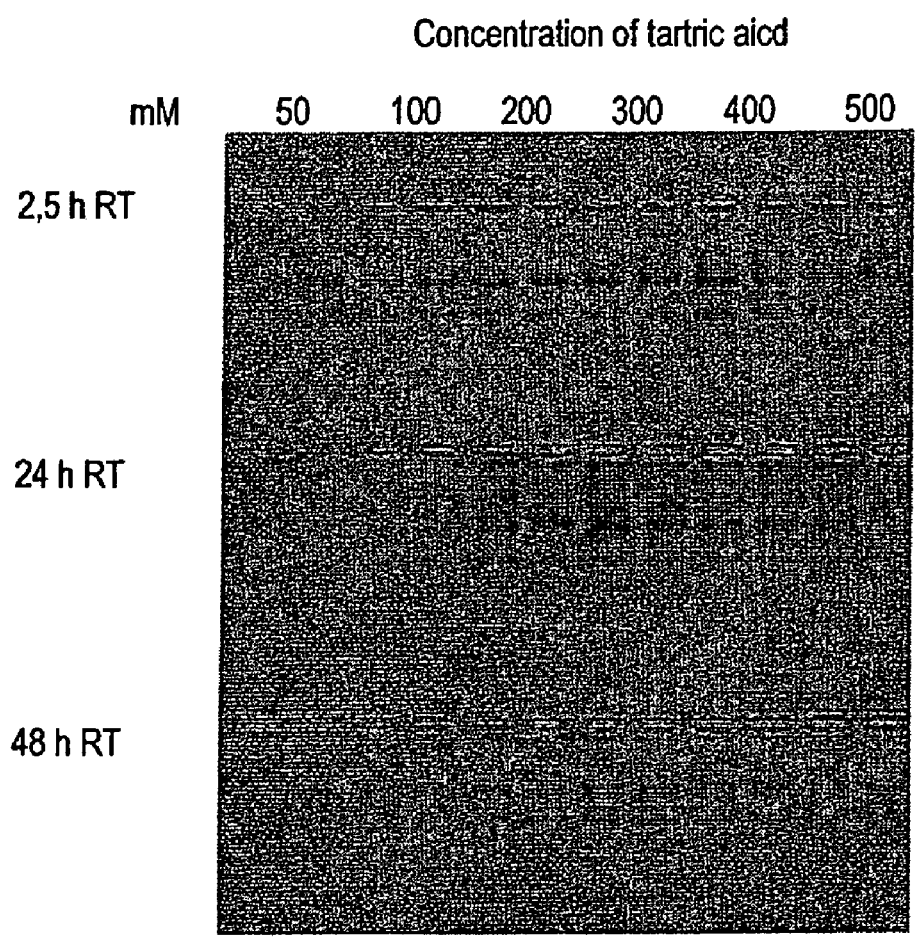
FIG. 2 shows the stabilisation of the RNA in whole blood by means of tetradecyltrimethyl ammonium oxalate, buffered with tartaric acid pH 3 in various concentrations.
Figure 4:
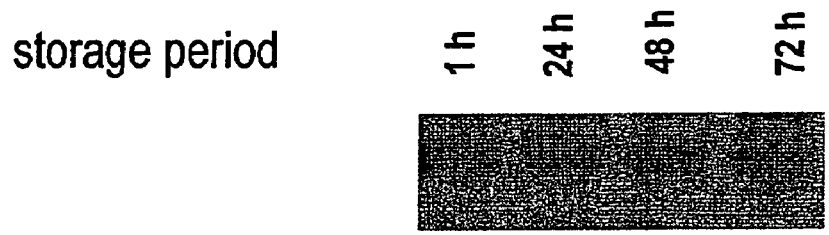
FIG. 4 shows the stabilisation of RNA in whole blood by means of tetradecyltrimethyl ammonium oxalate buffered with tartaric acid pH 3.7 as the result of Northern hybridisation with a radiolabelled probe for the mRNA of the GAPDH gene (A) and the IFN-γ gene (B). Even after storage for a period of 72 h, the mRNA of the GAPDH gene and of the IFN-γ gene can be detected in this experiment.
Figure 4:
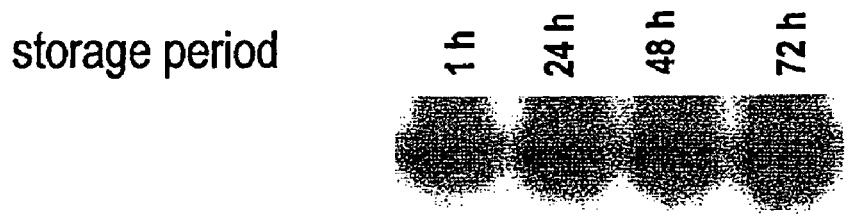

Northern Blot Analysis 2.5 ml of blood are mixed with 6.9 ml of a buffer consisting of 4% tetradecyltrimethyl ammonium oxalate and 200 mM tartaric acid pH 3.7 and stored for 1 h, 24 h, 48 h and 72 h at RT. To isolate the RNA the complexes of cationic compound and nucleic acid are centrifuged. The pellet is washed once with water and then taken up in 300 μl lysing buffer-for example buffer RLT made by QIAGEN. The rest of the sample preparation is carried out as described in FIG. 2. 2.5 μg aliquots of total RNA are then separated on a 1.2% denaturing agarose/formaldehyde gel. Then the RNA is transferred to a nylon membrane and hybridised over a period of about 12 h, in a sodium phosphate/SDS buffer, at 68° C., with a radiolabelled anti-sense RNA probe for the GAPDH gene (FIG. 4A), or the IFN-γ gene (FIG. 4B). The membrane is washed with washing buffers of decreasing salt concentration of 2×SSC/0.1% SDS to 0.1×SSC/0.1% SDS at a temperature of 68° C. The nylon membrane is then exposed on an X-ray film. Both the GAPDH and the IFN-γ-mRNA signal remains constant over a storage period of more than 72 h. This result shows that the mRNA has not broken down over this period.

Example 5

Stabilisation of the Genomic DNA in Blood by Means of Tetradecyltrimethyl Ammonium Oxalate Buffered with Tartaric Acid at pH 3.7

In addition to cellular RNA the genomic DNA from whole blood can also be stabilised by the method developed here and then isolated by binding to a silica membrane. FIG. 5 shows that even after storage for 72 h at RT high molecular DNA (length>20 kB) is isolated.

2.5 ml of blood are mixed with 6.9 ml of a solution consisting of 4% (w/v) of tetradecyltrimethyl ammonium oxalate and 200 mM tartaric acid at pH 3.7 and stored for 24 or 72 hours at RT. To isolate the DNA the complexes of cationic compound and DNA are centrifuged. The pellet is taken up in 300 μl of a buffer containing sodium chloride and EDTA, then 360 μl of a commercially obtainable guanidinium hydrochloride buffer—such as e.g. the buffer AL made by QIAGEN—as well as 20 μl of Proteinase K are added. The samples are incubated for 10 min at 65° C., then 420 μl ethanol are added and the sample is applied to a spin column containing a silica membrane. The sample is passed through the membrane by centrifugation. The silica membrane is washed with a standard commercial ethanol-containing guanidinium hydrochloride buffer—such as e.g. the buffer AW1 made by QIAGEN—and once with an ethanol-containing washing buffer—such as e.g. the buffer AW2 made by QIAGEN. The DNA is eluted with 300 μl of a Tris buffer (pH 8). 5 μl aliquots of the eluate are separated on an 0.8% agarose/TBE gel.

Example 6

Use of Genomic DNA in Enzymatic Reactions.

FIG. 6 shows that the DNA isolated according to Example 5 can be used for various enzymatic reactions (restriction and PCR amplification).

The DNA isolated after storage for 24 or 72 hours (see example 5) is used in various enzymatic reactions. This is evidence of the high purity and good quality of the isolated DNA.

A) 2: g aliquots of the DNA are cut with 6 U of the restriction enzymes EcoRI (E) and Hind III (H) for 3 hours at 37° C. and then separated on a 0.8% agarose/TBE gel. As a control the uncut DNA is applied.

B) 150 and 300 ng aliquots of the genomic DNA are used in a PCR reaction (total volume 50: 1) in which a 1.1 kB long fragment of the hugl gene is amplified. The PCR products are separated on a 1.2% agarose/TBE gel.

Example 7

RNA Stabilisation in Plasma by Means of Tetradecyltrimethyl Ammonium Oxalate Mixed with Various Additives These experiments demonstrate that the addition of carboxylic acids and other additives to tetradecyltrimethyl ammonium oxalate significantly improves the stabilisation of free RNA in plasma compared with RNA stabilisation using tetradecyltrimethyl ammonium oxalate on its own.

To prepare the solutions used in this experiment a stock solution of 30% tetradecyltrimethyl ammonium oxalate is mixed with a stock solution of 0.5 M of tartaric acid, citric acid, tartronic acid, succinic acid, ammonium sulphate or phosphoric acid to give a final concentration of 2% or 4% tetradecyltrimethyl ammonium oxalate and 200 mM of the additive. The stock solutions of the additives are adjusted to the specified pH with sodium hydroxide solution before being mixed with tetradecyltrimethyl ammonium oxalate. A 5% tetradecyltrimethyl ammonium oxalate solution without any additives is used as the control.

0.5 ml aliquots of every solution thus produced are placed in a 2 ml Eppendorf tube. 15: g of total RNA from HeLa cells, which is isolated beforehand, for example, by means of a commercially obtainable RNA isolation kit (e.g. the RNeasy® Maxi-Kits marketed as RNA isolation kits by QIAGEN) is pipetted into the lid of the Eppendorf container. 0.5 ml of human blood plasma is added to the solution, the lid of the container is closed and the container is quickly inverted five times to mix the fluids. The samples are stored for 1 day at RT (about 20 to 25° C.). All the experiments are carried out as double measurements.

To isolate the RNA the samples are centrifuged at 25000×g over a period of 3 min. The supernatant is removed and 0.5 ml of a buffer adjusted to 60° C., which contained guanidinium hydrochloride and Nonidet P40, pH 7.0, and also Proteinase K are added to the pellet. The pellet is dissolved by vortexing and incubated for 15 minutes at 50° C. Then 0.5 ml of an ethanol-nonidet P40 solution is added and the sample is mixed by vortexing for a period of about 5 seconds. The sample is then placed in a standard commercial spin column containing a silica membrane, such as for example the QIA amp columns made by QIAGEN, and passed through the membrane by centrifuging (1 min at 10000×g). The RNA remains bound to the membrane and is then washed twice with an alcohol-containing washing buffer, e.g. the buffer AW2 made by QIAGEN. The washing buffers are each passed through the membrane by centrifuging (1 min at 10000×g). After washing with the alcohol-containing washing buffer the membrane is dried by centrifuging (3 min max rpm, in this case 25000×g) without the addition of buffer. For elution, 30: 1 of RNase-free water are pipetted onto the membrane to detach the purified RNA from the membrane. The eluate is passed through the membrane by centrifuging (1 min at 10000×g) and the elution step is repeated once again to complete the elution process.

The isolated RNA is analysed on agarose gels stained with ethidium bromide. To do this, 1.0% formaldehyde-agarose-MOPS gels are prepared, for example. 30: 1 aliquots of the eluate are used. The results are shown in FIG. 7. The loading of the gel lanes is shown in Table 2.

TABLE 2

Summary of the samples illustrated in FIG. 7

| Sample No. | Final concentration of tetradecyltrimethyl ammonium oxalate | Additive |
|---|---|---|
| 1.2 | 4% | citric acid pH 4 |
| 3.4 | 4% | citric acid pH 5 |
| 5.6 | 4% | citric acid pH 6 |
| 7.8 | 4% | tartaric acid pH 3 |
| 9.10 | 4% | tartaric acid pH 4 |
| 11.12 | 4% | succinic acid pH 4 |
| 13.14 | 4% | tartronic acid pH 3 |
| 15.16 | 4% | tartronic acid pH 4 |
| 17.18 | 4% | phosphoric acid pH 3 |
| 19.20 | 4% | phosphoric acid pH 4 |
| 21.22 | 4% | phosphoric acid pH 5 |
| 23.24 | 2% | citric acid pH 3 |
| 25.26 | 2% | citric acid pH 4 |
| 27.28 | 2% | tartaric acid pH 3 |
| 29.30 | 2% | tartaric acid pH 4 |
| 31.32 | 2% | succinic acid pH 4 |
| 33.34 | 2% | phosphoric acid pH 2 |
| 35.36 | 2% | phosphoric acid pH 3 |
| 37.38 | 2% | phosphoric acid pH 4 |
| 39.40 | 2% | phosphoric acid pH 5 |
| 41.42 | 4% | ammonium sulphate pH 2 |
| 43.44 | 5% | — |

Lane 45 contains 3.75: g of the total RNA from HeLa cells used for these experiments in order to compare the RNA quality of the individual samples.

The separation by gel electrophoresis of the HeLa total RNA used for this experiment shows the intact 28S and 18S rRNA after staining with ethidium bromide. The topmost one of the visible rRNA bands (28S rRNA) is clearly more intense and thicker than the lower rRNA band (18S rRNA), which is a typical feature of intact undegraded RNA. A comparison of the HeLa total RNA stored for one day in plasma mixed with 5% of tetradecyltrimethyl ammonium oxalate without the addition of additive with the RNA which is isolated after one day's storage in plasma mixed with tetradecyltrimethyl ammonium oxalate and various additives clearly shows that the stabilisation of RNA is improved by the use of additives. If RNA is added to plasma without a stabilising compound, this leads to total breakdown of the RNA within a few minutes, as is well known.

Example 8

RNA Stabilisation in Plasma Using Tetradecyltrimethyl Ammonium Oxalate Mixed with Tartaric or Tartronic Acid Over Various Periods of Time.

These experiments show that the RNA is stabilised by mixtures of tetradecyltrimethyl ammonium oxalate and additive in plasma for up to at least 14 days.

To prepare the solutions used in this experiment a stock solution of 30% tetradecyltrimethyl ammonium oxalate is mixed with a stock solution of 0.5 M tartaric acid, pH 3 or tartronic acid pH 3 to give a final concentration of 6% or 8% tetradecyltrimethyl ammonium oxalate and 200 mM of the additive.

0.5 ml aliquots of every solution thus produced are placed in a 2 ml Eppendorf tube. 15: g of total RNA from HeLa cells, which is isolated beforehand, for example, by means of a commercially obtainable RNA isolation kit (e.g. the RNeasy® Maxi-Kits marketed by QIAGEN) is pipetted into the lid of the Eppendorf tube. 0.5 ml of human blood plasma is added to the solution, the lid of the container is closed and the tube is quickly inverted five times to mix the fluids. The samples are stored for 3, 7, 10 and 14 days at RT (about 20 to 25° C.). All the experiments are carried out as double measurements.

The RNA isolation is carried out as described in Example 7.

The isolated RNA is analysed on agarose gels stained with ethidium bromide. To do this, 1.0% formaldehyde-agarose-MOPS gels are prepared, for example. 30: 1 aliquots of the eluate are used. The results are shown in FIG. 8. The loading of the gel lanes is shown in Table 3.

TABLE 3

Summary of the samples shown in FIG. 8.

| Sample nos. | Concentration of tetradecyltrimethyl ammonium oxalate in the buffer | Additive | Storage period |
|---|---|---|---|
| 1.2 | 6% | tartaric acid pH 3 | 3 days |
| 3.4 | 8% | tartaric acid pH 3 | 3 days |
| 5.6 | 6% | tartronic acid pH 3 | 3 days |
| 7.8 | 8% | tartronic acid pH 3 | 3 days |
| 9.10 | 6% | tartaric acid pH 3 | 7 days |
| 11.12 | 8% | tartaric acid pH 3 | 7 days |
| 13.14 | 6% | tartronic acid pH 3 | 7 days |
| 15.16 | 8% | tartronic acid pH 3 | 7 days |
| 17.18 | 6% | tartaric acid pH 3 | 10 days |
| 19.20 | 8% | tartaric acid pH 3 | 10 days |
| 21.22 | 6% | tartronic acid pH 3 | 10 days |
| 23.24 | 8% | tartronic acid pH 3 | 10 days |
| 25.26 | 6% | tartaric acid pH 3 | 14 days |
| 27.28 | 8% | tartaric acid pH 3 | 14 days |
| 29.30 | 6% | tartronic acid pH 3 | 14 days |
| 31.32 | 8% | tartronic acid pH 3 | 14 days |

Lane "K" contains 3.75: g of the total RNA from HeLa cells used for these experiments in order to compare the RNA quality of the individual samples.

The separation by gel electrophoresis shows the intact 28S and 18S rRNA bands after staining with ethidium bromide, even after up to 14 days' storage of the HeLa total RNA in plasma mixed with tetradecyltrimethyl ammonium oxalate and tartaric acid or tartronic acid, pH 3.

Example 9

RNA Stabilisation in Plasma Using Tetradecyltrimethyl Ammonium Oxalate Mixed with Various Additives.

These experiments show that RNA can be stabilised by mixtures of tetradecyltrimethyl ammonium oxalate and additive even in large volumes of plasma.

To prepare the solutions used in this experiment a stock solution of 30% tetradecyltrimethyl ammonium oxalate is mixed with a stock solution of 0.5 M tartaric acid, pH 3 or 4, or tartronic acid, pH 3 or 4, or phosphoric acid at pH 3 or pH 4 to give a final concentration of 4% tetradecyltrimethyl ammonium oxalate and 200 mM of the additive.

1 ml aliquots of every solution thus produced are placed in a 2 ml Eppendorf tube. 15: g of total RNA from HeLa cells, which is isolated beforehand, for example, by means of the RNA isolation kit RNeasy® Maxi-Kits marketed by QIAGEN is pipetted into the lid of the Eppendorf tube. 1 ml of human blood plasma is added to the solution, the lid of the tube is closed and the tube is quickly inverted five times to mix the fluids. The samples are stored for 3 days at RT (about 20 to 25° C.). All the experiments are carried out as double measurements.

The RNA isolation is carried out as described in Example 7.

The isolated RNA is analysed on agarose gels stained with ethidium bromide. To do this, 1.0% formaldehyde-agarose-MOPS gels are prepared, for example. 30: 1 aliquots of the eluate are used. The results are shown in FIG. 9. The loading of the gel lanes is summarised in Table 4.

TABLE 4

Summary of the samples shown in FIG. 9

| Sample No. | Additive |
|---|---|
| 1.2 | tartaric acid pH 3 |
| 3.4 | tartaric acid pH 4 |
| 5.6 | phosphoric acid pH 3 |
| 7.8 | phosphoric acid pH 4 |
| 9.10 | tartronic acid pH 3 |
| 11.12 | tartronic acid pH 4 |

LANE 13 contains 3.75: g of the total RNA from HeLa cells used for these experiments in order to compare the RNA quality of the individual samples.

The separation by gel electrophoresis shows the intact 28S and 18S rRNA bands after staining with ethidium bromide. Thus, even in a large volume of plasma, RNA is stabilised by the mixture of tetradecyltrimethyl ammonium oxalate and additive.

Example 10

RNA Stabilisation in HeLa Cells Using Tetradecyltrimethyl Ammonium Oxalate Mixed with Various Additives.

These experiments show that RNA in HeLa cells can be stabilised by mixtures of tetradecyltrimethyl ammonium oxalate with various additives over a storage period of up to 14 days at RT.

To prepare the solutions used in this experiment a stock solution of 20% or 30% tetradecyltrimethyl ammonium oxalate is mixed with a stock solution of 0.5 M tartaric acid, citric acid, tartronic acid, ammonium sulphate or phosphoric acid to give a final concentration of 2% or 4% tetradecyltrimethyl ammonium oxalate and 200 mM of the additive. The stock solutions of the additives are adjusted to the specified pH with sodium hydroxide solution or sulphuric acid before being mixed with tetradecyltrimethyl ammonium oxalate.

$1\times10^6$ Hela cells which are harvested from the cell culture and washed with PBS immediately beforehand are pelleted by centrifuging (1 min at 120×g) and the supernatant is removed. 300 μl aliquots of the solutions listed in Table 4 are added to the cells and the samples are mixed by vortexing and the cells are re-suspended. The samples are stored for 3, 7, 10 and 14 days at RT (approx. 20 to 25° C.). All the experiments are carried out in the form of double measurements.

To isolate the RNA the cells are pelleted by centrifuging for three minutes at 1200×g and the supernatant is removed. The pellet is re-suspended in 600 μl of a standard commercial guanidinium isothiocyanate buffer—such as e.g. RLT buffer made by QIAGEN—by repeated pipetting up and down or by vortexing over a period of about 10 s or longer. Then 1 volume (600 μl) of 70% ethanol is added and the ingredients are mixed by repeated pipetting up and down or by vortexing over a period of about 5 s. The lysate is then applied to a standard commercial spin column containing a silica membrane—such as e.g. an RNeasy column made by QIAGEN-and passed through the membrane by centrifugation (1 min at 10000×g). The RNA remains bound to the membrane and is then washed with a first standard commercial guanidinium isothiocyanate-containing washing buffer—for example with the buffer RW1 made by QIAGEN—and then with a second alcohol-containing washing buffer, e.g. buffer RPE made by QIAGEN. The washing buffers are each passed through the membrane by centrifuging (1 min at 10000×g). The washing with the second alcohol-containing washing buffer is repeated with a smaller volume while the membrane is simultaneously dried by centrifugation (2 min max. rpm, in this case 20000×g). For elution, 40 μl of RNase-free water is pipetted onto the membrane in order to detach the purified RNA from the membrane. The eluate is passed through the membrane by centrifugation (1 min at 10000×g) and the elution step is repeated once more to complete the elution.

The isolated RNA is analysed on agarose gels stained with ethidium bromide. To do this, 1.0% formaldehyde-agarose-MOPS gels are prepared, for example. 20: 1 aliquots of the eluate are used. The results are shown in FIG. 10. The samples are summarised in Table 5, all the samples being tested and shown twice, with the exception of samples 14, 40, 66 and 92 which are tested and shown once.

TABLE 5

Summary of the samples shown in FIG. 10

| Sample No. | Final concentration of tetradecyl-trimethyl ammonium oxalate | Additive | final pH of the mixture of tetradecyl-trimethyl ammonium oxalate and additive approx. | Storage period |
|---|---|---|---|---|
| 1 | 4% | tartaric acid pH 3 | 3.4 | 3 days |
| 2 | 4% | tartaric acid pH 4 | 4.3 | 3 days |
| 3 | 4% | tartaric acid pH 5 | 5.3 | 3 days |
| 4 | 4% | tartaric acid pH 6 | 6.0 | 3 days |
| 5 | 4% | tartaric acid pH 7 | 7.3 | 3 days |
| 6 | 4% | phosphoric acid pH 3 | 4.3 | 3 days |
| 7 | 4% | phosphoric acid pH 4 | 4.9 | 3 days |
| 8 | 4% | phosphoric acid pH 5 | 6.0 | 3 days |
| 9 | 4% | phosphoric acid pH 6 | 6.3 | 3 days |
| 10 | 4% | phosphoric acid pH 7 | 7.1 | 3 days |
| 11 | 4% | ammonium sulphate pH 2 | 4.1 | 3 days |
| 12 | 4% | ammonium sulphate pH 3 | 5.2 | 3 days |
| 13 | 4% | ammonium sulphate pH 4 | 6.0 | 3 days |
| 14 | 4% | ammonium sulphate pH 5 | 6.1 | 3 days |
| 15 | 4% | citric acid pH 3 | 3.3 | 3 days |
| 16 | 4% | citric acid pH 4 | 4.3 | 3 days |
| 17 | 4% | citric acid pH 5 | 5.4 | 3 days |
| 18 | 4% | citric acid pH 6 | 6.3 | 3 days |
| 19 | 4% | citric acid pH 7 | 7.5 | 3 days |
| 20 | 4% | tartronic acid pH 3 | 3.6 | 3 days |
| 21 | 4% | tartronic acid pH 4 | 4.4 | 3 days |
| 22 | 4% | tartronic acid pH 5 | 5.3 | 3 days |
| 23 | 4% | tartronic acid pH 6 | 5.9 | 3 days |
| 24 | 4% | tartronic acid pH 7 | 7.3 | 3 days |
| 25 | 2% | tartaric acid pH 3 | nb | 3 days |
| 26 | 2% | tartaric acid pH 6 | nb | 3 days |
| 27 | 4% | tartaric acid pH 3 | 3.4 | 7 days |
| 28 | 4% | tartaric acid pH 4 | 4.3 | 7 days |
| 29 | 4% | tartaric acid pH 5 | 5.3 | 7 days |

TABLE 5-continued

Summary of the samples shown in FIG. 10

| Sample No. | Final concentration of tetradecyl-trimethyl ammonium oxalate | Additive | final pH of the mixture of tetradecyl-trimethyl ammonium oxalate and additive approx. | Storage period |
|---|---|---|---|---|
| 30 | 4% | tartaric acid pH 6 | 6.0 | 7 days |
| 31 | 4% | tartaric acid pH 7 | 7.3 | 7 days |
| 32 | 4% | phosphoric acid pH 3 | 4.3 | 7 days |
| 33 | 4% | phosphoric acid pH 4 | 4.9 | 7 days |
| 34 | 4% | phosphoric acid pH 5 | 6.0 | 7 days |
| 35 | 4% | phosphoric acid pH 6 | 6.3 | 7 days |
| 36 | 4% | phosphoric acid pH 7 | 7.1 | 7 days |
| 37 | 4% | ammonium sulphate pH 2 | 4.1 | 7 days |
| 38 | 4% | ammonium sulphate pH 3 | 5.2 | 7 days |
| 39 | 4% | ammonium sulphate pH 4 | 6.0 | 7 days |
| 40 | 4% | ammonium sulphate pH 5 | 6.1 | 7 days |
| 41 | 4% | citric acid pH 3 | 3.3 | 7 days |
| 42 | 4% | citric acid pH 4 | 4.3 | 7 days |
| 43 | 4% | citric acid pH 5 | 5.4 | 7 days |
| 44 | 4% | citric acid pH 6 | 6.3 | 7 days |
| 45 | 4% | citric acid pH 7 | 7.5 | 7 days |
| 46 | 4% | tartronic acid pH 3 | 3.6 | 7 days |
| 47 | 4% | tartronic acid pH 4 | 4.4 | 7 days |
| 48 | 4% | tartronic acid pH 5 | 5.3 | 7 days |
| 49 | 4% | tartronic acid pH 6 | 5.9 | 7 days |
| 50 | 4% | tartronic acid pH 7 | 7.3 | 7 days |
| 51 | 2% | tartaric acid pH 3 | nb | 7 days |
| 52 | 2% | tartaric acid pH 6 | nb | 7 days |
| 53 | 4% | tartaric acid pH 3 | 3.4 | 10 days |
| 54 | 4% | tartaric acid pH 4 | 4.3 | 10 days |
| 55 | 4% | tartaric acid pH 5 | 5.3 | 10 days |
| 56 | 4% | tartaric acid pH 6 | 6.0 | 10 days |
| 57 | 4% | tartaric acid pH 7 | 7.3 | 10 days |
| 58 | 4% | phosphoric acid pH 3 | 4.3 | 10 days |
| 59 | 4% | phosphoric acid pH 4 | 4.9 | 10 days |
| 60 | 4% | phosphoric acid pH 5 | 6.0 | 10 days |
| 61 | 4% | phosphoric acid pH 6 | 6.3 | 10 days |
| 62 | 4% | phosphoric acid pH 7 | 7.1 | 10 days |
| 63 | 4% | ammonium sulphate pH 2 | 4.1 | 10 days |
| 64 | 4% | ammonium sulphate pH 3 | 5.2 | 10 days |
| 65 | 4% | ammonium sulphate pH 4 | 6.0 | 10 days |
| 66 | 4% | ammonium sulphate pH 5 | 6.1 | 10 days |
| 67 | 4% | citric acid pH 3 | 3.3 | 10 days |
| 68 | 4% | citric acid pH 4 | 4.3 | 10 days |
| 69 | 4% | citric acid pH 5 | 5.4 | 10 days |
| 70 | 4% | citric acid pH 6 | 6.3 | 10 days |
| 71 | 4% | citric acid pH 7 | 7.5 | 10 days |
| 72 | 4% | tartronic acid pH 3 | 3.6 | 10 days |
| 73 | 4% | tartronic acid pH 4 | 4.4 | 10 days |
| 74 | 4% | tartronic acid pH 5 | 5.3 | 10 days |
| 75 | 4% | tartronic acid pH 6 | 5.9 | 10 days |
| 76 | 4% | tartronic acid pH 7 | 7.3 | 10 days |
| 77 | 2% | tartaric acid pH 3 | nb | 10 days |
| 78 | 2% | tartaric acid pH 6 | nb | 10 days |
| 79 | 4% | tartaric acid pH 3 | 3.4 | 14 days |
| 80 | 4% | tartaric acid pH 4 | 4.3 | 14 days |
| 81 | 4% | tartaric acid pH 5 | 5.3 | 14 days |
| 82 | 4% | tartaric acid pH 6 | 6.0 | 14 days |
| 83 | 4% | tartaric acid pH 7 | 7.3 | 14 days |
| 84 | 4% | phosphoric acid pH 3 | 4.3 | 14 days |
| 85 | 4% | phosphoric acid pH 4 | 4.9 | 14 days |
| 86 | 4% | phosphoric acid pH 5 | 6.0 | 14 days |
| 87 | 4% | phosphoric acid pH 6 | 6.3 | 14 days |
| 88 | 4% | phosphoric acid pH 7 | 7.1 | 14 days |
| 89 | 4% | ammonium sulphate pH 2 | 4.1 | 14 days |
| 90 | 4% | ammonium sulphate pH 3 | 5.2 | 14 days |
| 91 | 4% | ammonium sulphate pH 4 | 6.0 | 14 days |
| 92 | 4% | ammonium sulphate pH 5 | 6.1 | 14 days |
| 93 | 4% | citric acid pH 3 | 3.3 | 14 days |
| 94 | 4% | citric acid pH 4 | 4.3 | 14 days |
| 95 | 4% | citric acid pH 5 | 5.4 | 14 days |
| 96 | 4% | citric acid pH 6 | 6.3 | 14 days |
| 97 | 4% | citric acid pH 7 | 7.5 | 14 days |
| 98 | 4% | tartronic acid pH 3 | 3.6 | 14 days |
| 99 | 4% | tartronic acid pH 4 | 4.4 | 14 days |
| 100 | 4% | tartronic acid pH 5 | 5.3 | 14 days |
| 101 | 4% | tartronic acid pH 6 | 5.9 | 14 days |
| 102 | 4% | tartronic acid pH 7 | 7.3 | 14 days |
| 103 | 2% | tartaric acid pH 3 | nb | 14 days |
| 104 | 2% | tartaric acid pH 6 | nb | 14 days |

The samples "K" show total RNA which is isolated from $1\times10^6$ Hela cells (=positive control) by means of an isolation kit such as, for example, the RNeasy® Mini Kits made by QIAGEN, without previously being stored. The samples "a", "b", "c" and "d" show a total RNA which is isolated after 3, 7, 10 or 14 days' storage of $1\times10^6$ Hela cells in PBS—without additives—as described above.

The amount of isolated total RNA is determined after dilution in water by photometric measurement of light absorption at a wavelength of 260 nm. The purity of the RNA thus obtained is determined by photometrically determining the ratio of light absorption at 260 nm to that at 280 nm. The results of the isolations are shown in Table 6 that follows. In each case the averages of the two measurements are given.

TABLE 6

RNA yield of the total RNA isolated according to Example 10 from HeLa cells stored in tetradecyltrimethyl ammonium oxalate mixed with various additives

| Additive | Storage period (days) | RNA Yield (µg) | $E_{260}/E_{280}$ |
|---|---|---|---|
| tartaric acid pH 5 | 3 | 28.7 | 1.84 |
| tartaric acid pH 5 | 7 | 30.7 | 1.86 |
| tartaric acid pH 5 | 10 | 33.4 | 1.90 |

TABLE 6-continued

RNA yield of the total RNA isolated according to Example 10 from HeLa cells stored in tetradecyltrimethyl ammonium oxalate mixed with various additives

| Additive | Storage period (days) | RNA Yield (µg) | $E_{260}/E_{280}$ |
|---|---|---|---|
| tartaric acid pH 5 | 14 | 56.4 | 1.94 |
| tartaric acid pH 6 | 3 | 38.4 | 1.92 |
| tartaric acid pH 6 | 7 | 55.5 | 2.0 |
| tartaric acid pH 6 | 10 | 36.1 | 1.93 |
| tartaric acid pH 6 | 14 | 36.9 | 1.94 |
| phosphoric acid pH 5 | 3 | 39.5 | 1.89 |
| phosphoric acid pH 5 | 7 | 27.1 | 1.91 |
| phosphoric acid pH 5 | 10 | 36.9 | 1.89 |
| phosphoric acid pH 5 | 14 | 40.2 | 1.85 |
| phosphoric acid pH 6 | 3 | 25.6 | 1.98 |
| phosphoric acid pH 6 | 7 | 29.2 | 1.89 |
| phosphoric acid pH 6 | 10 | 34..2 | 1.88 |
| phosphoric acid pH 6 | 14 | 40.9 | 1.95 |
| tartronic acid pH 5 | 3 | 24.7 | 1.95 |
| tartronic acid pH 5 | 7 | 30.8 | 1.91 |
| tartronic acid pH 5 | 10 | 30.4 | 1.90 |
| tartronic acid pH 5 | 14 | 30.8 | 1.95 |
| tartronic acid pH 6 | 3 | 30.6 | 1.96 |
| tartronic acid pH 6 | 7 | 31.0 | 1.90 |
| tartronic acid pH 6 | 10 | 34.0 | 1.95 |
| tartronic acid pH 6 | 14 | 32.0 | 1.92 |
| ammonium sulphate pH 5 | 3 | 31.5 | 1.98 |
| ammonium sulphate pH 5 | 7 | 27.1 | 1.88 |
| ammonium sulphate pH 5 | 10 | 35.7 | 1.93 |
| ammonium sulphate pH 5 | 14 | 35.5 | 1.92 |
| citric acid pH 6 | 3 | 24.4 | 1.91 |
| citric acid pH 6 | 7 | 31.5 | 1.94 |
| citric acid pH 6 | 10 | 32.5 | 1.94 |
| citric acid pH 6 | 14 | 39.2 | 1.94 |
| Positive control | 0 | 33.2 | 1.90 |

The separation by gel electrophoresis shows the intact 28S and 18S rRNA bands in the positive controls after staining with ethidium bromide. The topmost one of the rRNA bands (28S rRNA) is clearly more intense and thicker than the lower rRNA band (18S rRNA), which is a typical feature of intact undegraded RNA. After 3 days' storage of the cells in PBS the RNA is partly degraded as the two rRNA bands exhibit the same intensity and significantly less RNA is visible. After 7 days' storage or longer, no more RNA is visible. By contrast, the RNA in Hela cells is stabilised by tetradecyltrimethyl ammonium oxalate mixed with various additives for up to 14 days. This is confirmed by OD measurement of a specific RNA yield and purity. The stabilisation is influenced by the pH. Final pH values of more than 4 are preferred in the mixture, i.e. after the mixing of tetradecyltrimethyl ammonium oxalate and additive.

Example 11

RNA Stabilisation in Different Amounts of Hela Cells

These experiments show that RNA in HeLa cells can be stabilised by mixtures of tetradecyltrimethyl ammonium oxalate with additives irrespective of the number of cells used.

To prepare the solution used in this experiment a stock solution of 20% tetradecyltrimethyl ammonium oxalate is mixed with a stock solution of 0.5 M tartaric acid at pH 6 to give a final concentration of 4% tetradecyltrimethyl ammonium oxalate and 200 mM of the additive. The stock solution of the additive is adjusted to the specified pH with sodium hydroxide solution before being mixed with tetradecyltrimethyl ammonium oxalate.

$1 \times 10^5$, $5 \times 10^5$, $1 \times 10^6$ and $5 \times 10^6$ Hela cells which are harvested from the cell culture and washed with PBS immediately beforehand are pelleted by centrifuging (1 min at 120×g) and the supernatant is removed. 300 µl aliquots of the solution containing 4% tetradecyltrimethyl ammonium oxalate and 200 mM of tartaric acid are added to the cells and the samples are mixed by vortexing and the cells are re-suspended. The samples are stored for 15 min or 1 day at RT (approx. 20 to 25° C.). All the experiments are carried out in the form of double measurements.

The RNA is isolated as described in Example 10.

The controls used are $1 \times 10^5$, $5 \times 10^5$, $1 \times 10^6$ and $5 \times 10^6$ Hela cells which have not been pre-treated with 4% tetradecyltrimethyl ammonium oxalate, 200 mM tartaric acid and have not been stored to isolate the RNA as described above.

The isolated RNA is analysed on agarose gels stained with ethidium bromide. To do this, 1.0% formaldehyde-agarose-MOPS gels are prepared, for example. 20: 1 aliquots of the eluate are used. The results are shown in FIG. 11. The samples are summarised in Table 7, all the samples being tested and shown twice.

TABLE 7

Summary of the samples shown in FIG. 11

| Sample No. | cell count | storage |
|---|---|---|
| 1.2 | $1 \times 10^5$ | — |
| 3.4 | $1 \times 10^5$ | 15 min |
| 5.6 | $1 \times 10^5$ | 1 day |
| 7.8 | $5 \times 10^5$ | — |
| 9.10 | $5 \times 10^5$ | 15 min |
| 11.12 | $5 \times 10^5$ | 1 day |
| 13.14 | $1 \times 10^6$ | — |
| 15.16 | $1 \times 10^6$ | 15 min |
| 17.18 | $1 \times 10^6$ | 1 day |
| 19.20 | $5 \times 10^6$ | — |
| 21.22 | $5 \times 10^6$ | 15 min |
| 23.24 | $5 \times 10^6$ | 1 day |

The amount of isolated total RNA is determined after dilution in water by photometrically measuring the light absorption at a wavelength of 260 nm. The purity of the RNA thus obtained is determined by photometrically determining the ratio of light absorption at 260 nm to that at 280 nm. The results of the isolations are shown in Table 8 that follows. In each case the averages of the two measurements are given.

TABLE 8

RNA yield of total RNA isolated according to Example 11 from Hela cells stored in 4% tetradecyl-trimethylammonium oxalate, 200 mM tartaric acid

| cell count | storage | RNA yield (µg) | $E_{260}/E_{280}$ |
|---|---|---|---|
| $1 \times 10^5$ | — | 3.0 | 2.04 |
| $1 \times 10^5$ | 15 min | 3.1 | 1.92 |
| $1 \times 10^5$ | 1 day | 3.5 | 1.97 |
| $5 \times 10^5$ | — | 16.2 | 1.83 |
| $5 \times 10^5$ | 15 min | 15.2 | 1.85 |
| $5 \times 10^5$ | 1 day | 16.0 | 1.86 |
| $1 \times 10^6$ | — | 28.2 | 1.75 |
| $1 \times 10^6$ | 15 min | 28.2 | 1.73 |
| $1 \times 10^6$ | 1 day | 34.4 | 1.77 |
| $5 \times 10^6$ | — | 107.3 | 1.64 |
| $5 \times 10^6$ | 15 min | 91.3 | 1.61 |
| $5 \times 10^6$ | 1 day | 122.6 | 1.61 |

The separation by gel electrophoresis shows the intact 28S and 18S rRNA bands in the stored control samples and also in the non-stored control samples after staining with ethidium bromide. There is no apparent difference between the non-stored controls and the stored samples. Similarly, the RNA yield and purity determined by OD measurement confirms that the stabilisation of the RNA takes place to the same extent in different quantities of cells without reducing the yields or purity of the RNA. The $E_{260}/E_{280}$ quotients which decrease as the cell count increases can be put down to the fact that the measurements were carried out in water and not in a buffered system.

Example 12

RNA Stabilisation in Macrophages

These experiments demonstrate that RNA can be used in different types of cells. The macrophages used in this experiment contain more RNases than the Hela cells used previously, thus forcing the breakdown of RNA in the cells.

To prepare the solutions used in this experiment a stock solution of 20% tetradecyltrimethyl ammonium oxalate is mixed with a stock solution of 0.5 M tartaric acid pH 5, 0.5 M tartronic acid pH 5 or 0.5 M phosphoric acid pH 5 to give a final concentration of 4% tetradecyltrimethyl ammonium oxalate and 200 mM of the additive. The stock solution of the additive is adjusted to the specified pH with sodium hydroxide solution before being mixed with tetradecyltrimethyl ammonium oxalate.

$1 \times 10^6$ Hela cells which are harvested from the cell culture and washed with PBS immediately beforehand are pelleted by centrifuging (1 min at 120×g) and the supernatant is removed. 300 μl aliquots of the solution containing 4% tetradecyltrimethyl ammonium oxalate and 200 mM of additive are added to the cells and the cells are re-suspended. The samples are stored for 2 days, 6 days, 9 days and 14 days at RT (approx. 20 to 25° C.). All the experiments are carried out in the form of double measurements.

The RNA is isolated as described in Example 10.

The isolated RNA is analysed on agarose gels stained with ethidium bromide. To do this, 1.0% formaldehyde-agarose-MOPS gels are prepared, for example. 20:1 aliquots of the eluate are used. The results are shown in FIG. 12. The samples are summarised in Table 9, all the samples being tested and shown twice.

TABLE 9

Summary of the samples shown in FIG. 12

| Sample No. | Additive | storage |
|---|---|---|
| 1.2 | 200 mM phosphoric acid pH 5 | 2 days |
| 3.4 | 200 mM phosphoric acid pH 5 | 6 days |
| 5.6 | 200 mM phosphoric acid pH 5 | 9 days |
| 7.8 | 200 mM phosphoric acid pH 5 | 14 days |
| 9.10 | 200 mM tartronic acid pH 5 | 2 days |
| 11.12 | 200 mM tartronic acid pH 5 | 6 days |
| 13.14 | 200 mM tartronic acid pH 5 | 9 days |
| 15.16 | 200 mM tartronic acid pH 5 | 14 days |
| 17.18 | 200 mM tartaric acid pH 5 | 2 days |
| 19.20 | 200 mM tartaric acid pH 5 | 6 days |
| 21.22 | 200 mM tartaric acid pH 5 | 9 days |
| 23.24 | 200 mM tartaric acid pH 5 | 14 days |

Lanes 25 and 26 show a total RNA which is isolated from $1 \times 10^6$ macrophages (=positive control) without previous storage of the macrophages, using a commercially obtainable isolation kit such as e.g. RNeasy® Mini Kits made by QIAGEN.

The amount of isolated total RNA is determined after dilution in water by photometric measurement of light absorption at a wavelength of 260 nm. The purity of the RNA thus obtained is determined by photometrically determining the ratio of light absorption at 260 nm to that at 280 nm. The results of the isolations are shown in Table 10 that follows. In each case the averages of the two measurements are given.

TABLE 10

Yield of nucleic acid from the macrophages stored according to Example 12 in 4% tetradecyltrimethyl ammonium oxalate, 200 mM additive

| Additive | storage | RNA yield (μg) | $E_{260}/E_{280}$ |
|---|---|---|---|
| 200 mM phosphoric acid pH 5 | 2 days | 24.2 | 1.91 |
| 200 mM phosphoric acid pH 5 | 6 days | 25.7 | 1.86 |
| 200 mM phosphoric acid pH 5 | 9 days | 21.6 | 1.83 |
| 200 mM phosphoric acid pH 5 | 14 days | 23.5 | 1.83 |
| 200 mM tartronic acid pH 5 | 2 days | 241 | 1.86 |
| 200 mM tartronic acid pH 5 | 6 days | 23.2 | 1.85 |
| 200 mM tartronic acid pH 5 | 9 days | 20.2 | 1.86 |
| 200 mM tartronic acid pH 5 | 14 days | 27.8 | 1.81 |
| 200 mM tartaric acid pH 5 | 2 days | 25.4 | 1.85 |
| 200 mM tartaric acid pH 5 | 6 days | 30.9 | 1.84 |
| 200 mM tartaric acid pH 5 | 9 days | 24.3 | 1.86 |
| 200 mM tartaric acid pH 5 | 14 days | 25.1 | 1.86 |
| Positive control | no storage | 16.3 | 1.88 |

The separation by gel electrophoresis shows the intact 28S and 18S rRNA bands in the stored control samples and also in the non-stored control samples after staining with ethidium bromide, while even after 14 days' storage there is no sign of RNA degradation. Similarly, the yields and purities of RNA determined by photometric measurement remain unchanged during storage.

Example 13

RNA Stabilisation in Adherent Hela Cells without Removal of the Medium

These experiments show that RNA can be stabilised even in adherent cells by mixtures of tetradecyltrimethyl ammonium oxalate and additive. The stabilisation still takes place even when the medium containing the cells is not removed but instead the mixture of tetradecyltrimethyl ammonium oxalate and additive is added to the medium. Cells in medium may be regarded as a model of cells in body fluids.

To prepare the solutions used in this experiment, tetradecyltrimethyl ammonium oxalate and the particular additive, tartaric acid or ammonium sulphate, are weighed out to give a final concentration of 4% tetradecyltrimethyl ammonium oxalate and 200 mM additive, and dissolved in water. The pH of the solution is adjusted to pH 5 with sodium hydroxide solution in the case of 4% tetradecyltrimethyl ammonium oxalate, 200 mM tartaric acid and with sulphuric acid in the case of 4% tetradecyltrimethyl ammonium oxalate, 200 mM ammonium sulphate.

Hela cells are cultured in 6-well plates in 2 ml of medium. The cells grow adherently, i.e. they adhere to the bottom of the well. To stabilise the RNA in the cells, 10 ml of 4% tetradecyltrimethyl ammonium oxalate, 200 mM tartaric acid pH 5 or 4% tetradecyltrimethyl ammonium oxalate, 200 mM ammonium sulphate pH 5 are added to each well and the dishes are stored for 4 days at RT. As a negative control a well containing medium but without the addition of the mixture of 4% tetradecyltrimethyl ammonium oxalate and 200 mM additive is stored for 4 days at RT.

As a positive control the RNA of the Hela cells from one well is isolated without prior storage using a standard commercial isolation kit, such as e.g. RNeasy® Mini Kits made by QIAGEN. To do this the medium is totally removed from the cells and combined with 350 μl of the lysing buffer RLT (ingredient of the RNeasy Kit). The cells are scraped off the bottom of the well with a spatula and the lysate is transferred into a so-called shredder, such as e.g. the QIAshredder made by QIAGEN. By centrifuging for 2 min at 14000 rpm the lysate is passed through the shredder and in this way the sample is homogenised. The product is mixed with 70% ethanol and the RNA is isolated as described in Example 10.

After the cells have been stored for 4 days in a medium mixed with 4% tetradecyltrimethyl ammonium oxalate, 200 mM additive, the now detached cells are completely taken up together with the supernatant and centrifuged for 5 min at 3000×g. The supernatants are removed and the cell pellet is used to isolate the RNA as described in Example 10.

After the cells have been stored for 4 days in a medium without 4% tetradecyltrimethyl ammonium oxalate, 200 mM additive (=negative control) the RNA is isolated as described above for the positive control.

The isolated RNA is analysed on agarose gels stained with ethidium bromide. To do this, 1.0% formaldehyde-agarose-MOPS gels are prepared, for example. 20: 1 aliquots of the eluate are used. The results are shown in FIG. 13. Lane 1 contains total RNA which is isolated after the cells have been stored in medium mixed with 4% tetradecyltrimethyl ammonium oxalate, 200 mM tartaric acid, pH 5. Lane 2 shows total RNA which is isolated after the cells have been stored in medium mixed with 4% tetradecyltrimethyl ammonium oxalate, 200 mM ammonium phosphate, at pH 5. Lane 3 shows a total RNA which is isolated after the cells have been stored in medium alone and lane 4 shows a total RNA which is isolated as a positive control without being stored beforehand.

The amount of isolated total RNA is determined after diluting in water by photometrically measuring the light absorption at a wavelength of 260 nm. The purity of the RNA thus obtained is measured by photometrically determining the ratio of light absorption at 260 nm to that at 280 nm. The results of the isolations are given in Table 11 below.

TABLE 11

RNA yield of the total RNA isolated from adherent Hela cells according to Example 13.

| Storage in medium mixed with | RNA yield (μg) | $E_{260}/E_{280}$ |
| --- | --- | --- |
| 4% tetradecyltrimethyl ammonium oxalate, 200 mM tartaric acid, pH 5 | 10.9 | 1.70 |
| 4% tetradecyltrimethyl ammonium oxalate, 200 mM ammonium sulphate, pH 5 | 13.2 | 1.75 |
| — | 6.1 | 1.58 |
| positive control without storage | 12.5 | 1.75 |

The separation by gel electrophoresis shows the intact 28S and 18S rRNA in the non-stored sample and also in the samples stored with mixtures of tetradecyltrimethyl ammonium oxalate and additive, after staining with ethidium bromide. By contrast, the RNA in the cells which are stored in medium without the addition of tetradecyltrimethyl ammonium oxalate and additive is almost totally broken down. Similarly, the RNA yield and purity determined by OD measurement confirms that there is no difference between non-stored samples and stabilised samples, whereas the yield and purity of the RNA in the samples stored in medium without the addition of tetradecyltrimethyl ammonium oxalate and additive is significantly reduced.

Example 14

RNA Stabilisation in Tissue by Means of Tetradecyltrimethyl Ammonium Oxalate Mixed with Various Additives These experiments show that tetradecyltrimethyl ammonium oxalate mixed with various additives is also suitable for stabilising RNA from tissue.

To prepare the solutions used in this experiment a stock solution of 20% tetradecyltrimethyl ammonium oxalate is mixed with a stock solution of 0.5 M of tartaric acid, citric acid, tartronic acid, ammonium sulphate, potassium phosphate, oxalic acid or phosphoric acid to give a final concentration of 4% tetradecyltrimethyl ammonium oxalate and 200 mM of the additive. The stock solutions of the additives are adjusted to the specified pH with sodium hydroxide solution or sulphuric acid (or ammonium sulphate) or potassium hydroxide solution or phosphoric acid (or potassium phosphate) before being mixed with tetradecyltrimethyl ammonium oxalate.

Kidney tissue from mice, which has been frozen in liquid nitrogen immediately after being removed and then stored at −70° C., is used for these experiments. 70 to 90 mg of the tissue are frozen, 500 μl of the buffers specified in Table 12 are added for each 10 mg of tissue and the mixture is homogenised immediately using a rotor-stator homogeniser—such as e.g. the Polytron made by Messrs Kinematica—for 30 to 60 s. 500 μl aliquots of solution are taken from the homogenised preparations, corresponding to 10 mg of tissue. The samples are stored for one day at RT.

After storage the samples are centrifuged for 3 min at 10000×g and the supernatant is removed. The pellet is dissolved completely in 600 μl of a standard commercial guanidinium isothiocyanate buffer—such as e.g. RLTbuffer made by QIAGEN—by vortexing. Then 1 volume (600 μl) of 70% ethanol is added and the ingredients are mixed by repeated pipetting up and down or by vortexing over a period of about 5 s. The lysate is then applied to a standard commercial spin column containing a silica membrane—such as e.g. an RNeasy column made by QIAGEN—and passed through the membrane by centrifugation (1 min at 10000×g). The RNA remains bound to the membrane and is then washed with a first standard commercial guanidinium isothiocyanate-containing washing buffer—for example with the buffer RW1 made by QIAGEN—and then with a second alcohol-containing washing buffer, e.g. buffer RPE made by QIAGEN. The washing buffers are each passed through the membrane by centrifuging (1 min at 10000×g). The washing with the second alcohol-containing washing buffer is repeated with a smaller volume while the membrane is simultaneously dried by centrifugation (2 min max. rpm, in this case 20000×g). For elution, 40 μl of RNase-free water is pipetted onto the membrane in order to detach the purified RNA from the membrane. The eluate is passed through the membrane by centrifugation (1 min at 10000×g) and the elution step is repeated once more to complete the elution.

The isolated RNA is analysed on agarose gels stained with ethidium bromide. To do this, 1.0% formaldehyde-agarose-MOPS gels are prepared, for example. 20: 1 aliquots of the eluate are used. The results are shown in FIG. 14. The samples are summarised in Table 12, all the samples being experimented on and shown twice.

TABLE 12

Summary of the samples shown in FIG. 14

| Sample No. | Additive | pH of the additive | final pH of the mixture of tetradecyltrimethyl ammonium oxalate and additive |
|---|---|---|---|
| 1 | tartaric acid | 3 | 3.4 |
| 2 | tartaric acid | 4 | 4.3 |
| 3 | tartaric acid | 5 | 5.3 |
| 4 | tartaric acid | 6 | 6.0 |
| 5 | tartaric acid | 7 | 7.3 |
| 6 | citric acid | 3 | 3.3 |
| 7 | citric acid | 4 | 4.3 |
| 8 | citric acid | 5 | 5.4 |
| 9 | citric acid | 6 | 6.3 |
| 10 | citric acid | 7 | 7.5 |
| 11 | oxalic acid | 4 | 4.3 |
| 12 | oxalic acid | 5 | 5.3 |
| 13 | oxalic acid | 6.17 | 6.5 |
| 14 | oxalic acid | 7 | 7.2 |
| 15 | phosphoric acid | 3 | 4.3 |
| 16 | phosphoric acid | 4 | 4.9 |
| 17 | phosphoric acid | 5 | 6.0 |
| 18 | phosphoric acid | 6 | 6.3 |
| 19 | phosphoric acid | 7 | 7.1 |
| 20 | potassium phosphate | 4.2 | 4.9 |
| 21 | potassium phosphate | 5 | 5.3 |
| 22 | potassium phosphate | 6 | 6.1 |
| 23 | potassium phosphate | 7 | 6.9 |
| 24 | potassium phosphate | 8 | 7.8 |
| 25 | tartronic acid | 3 | 3.6 |
| 26 | tartronic acid | 4 | 4.4 |
| 27 | tartronic acid | 5 | 5.3 |
| 28 | tartronic acid | 6 | 5.9 |
| 29 | tartronic acid | 7 | 7.3 |
| 30 | ammonium sulphate | 2 | 4.1 |
| 31 | ammonium sulphate | 3 | 5.2 |
| 32 | ammonium sulphate | 4 | 6.0 |
| 33 | ammonium sulphate | 5 | 6.1 |

The samples "K" show total RNA which is isolated from 10 mg of frozen kidney issue (=positive control) by means of an isolation kit (RNeasy made total QIAGEN GmbH) without previously being stored. The lanes "N" show a total RNA which is isolated after one day's storage of 10 mg of kidney tissue dry, i.e. without the addition of solvent, using the RNeasy® Mini Kit made by QIAGEN (=negative control.)

The separation by gel electrophoresis shows the intact 28S and 18S rRNA bands in the positive control after staining with ethidium bromide. The negative control, comprising kidney tissue stored without stabilising solution, shows totally degraded RNA. By contrast, after the samples have been stored in tetradecyltrimethyl ammonium oxalate mixed with various additives, the intact rRNA bands are visible as in the positive control. The stabilisation is influenced by the pH. Final pH values of more than 4 are preferred in the stabilising solution after the mixing of tetradecyltrimethyl ammonium oxalate and additive of a specified pH, for stabilising RNA in tissue.

Example 15

DNA Stabilisation and Isolation Parallel to RNA Stabilisation and Isolation

These experiments show that not only RNA but also DNA in tissue is stabilised using tetradecyltrimethyl ammonium oxalate mixed with various additives. In addition to isolating RNA from a sample, it is also possible to isolate DNA in parallel thereto.

To prepare the solutions used in this experiment a stock solution of 20% tetradecyltrimethyl ammonium oxalate is mixed with a stock solution of 0.5 M of citric acid, pH 5, adjusted with sodium hydroxide solution to give a final concentration of 4% tetradecyltrimethyl ammonium oxalate and 200 mM of the additive.

Kidney tissue from mice, which has been frozen in liquid nitrogen immediately after being removed and then stored at −70° C., is used for these experiments. About 80 mg of the tissue are frozen, 4.2 ml of 4% tetradecyltrimethyl ammonium oxalate, 200 mM of citric acid pH 5 are added for each 10 mg of tissue and the mixture is homogenised immediately using a rotor-stator homogeniser such as e.g. the Polytron made by Messrs Kinematica for 30 to 60 s. 500 µl aliquots of solution are taken from the homogenised preparation, corresponding to 10 mg of tissue. The samples are stored for one day at RT.

After storage the samples are centrifuged for 3 min at 10000×g and the supernatant is removed. The pellet is dissolved completely in 600 µl of a standard commercial guanidinium isothiocyanate buffer—such as e.g. RLT buffer made by QIAGEN—by vortexing. Then 1 volume (600 µl) of 70% ethanol is added and the ingredients are mixed by repeated pipetting up and down or by vortexing over a period of about 5 s. The lysate is then applied to a standard commercial spin column containing a silica membrane—such as e.g. an RNeasy column made by QIAGEN—and passed through the membrane by centrifugation (1 min at 10000×g). The RNA remains bound to the membrane and can then be isolated as described in Example 14. The throughflow (about 1200 µl) is collected and combined with 200 µl of 100% ethanol and mixed by vortexing. These samples are again applied to a standard commercial spin column containing a silica membrane, such as, for example, a QIAamp column made by QIAGEN, and passed through the membrane by centrifugation (1 min at 10000×g). The DNA remains bound to the membrane and is then washed with a first standard commercial guanidinium isothiocyanate-containing washing buffer—for example with the buffer RW1 made by QIAGEN—and then with a second alcohol-containing washing buffer, e.g. buffer RPE made by QIAGEN. The washing buffers are each passed through the membrane by centrifuging (1 min at 10000×g). The washing with the second alcohol-containing washing buffer is repeated with a smaller volume while the membrane is simultaneously dried by centrifugation (2 min max. rpm, in this case 20000×g). For elution, 200 µl of water is pipetted onto the membrane and incubated for 1 min at RT to detach the purified DNA from the membrane. The eluate is passed through the membrane by centrifugation (1 min at 10000×g) and the elution step is repeated once more to complete the elution.

The isolated RNA is analysed on agarose gels stained with ethidium bromide. To do this, 0.8% agarose-TBE gels are prepared, for example. 40:1 aliquots of samples 1 to 4 and 20:1 aliquots of samples 5 to 9 are used. The results are shown in FIG. 15.

Lanes 1 and 2 show the total DNA isolated according to Example 15. Lanes 3 and 4 show 0.1 µg and 0.5 µg, respectively, of a total DNA as reference, to demonstrate the flow characteristics of an intact genomic DNA in the agarose gel used. Lane 5 shows a total DNA isolated from 10 mg of frozen rat's kidney (=positive control) using a commercially obtainable isolation kit (QIAamp® Mini Kits of Messrs QIAGEN GmbH) without being stored beforehand. The negative control used was total DNA which is isolated, after one day's storage, from 10 mg of kidney tissue dry, i.e. without the addition of solvent, or in distilled water, using the QIAamp® Mini Kits made by QIAGEN. This DNA is shown in lanes 6 and 7 (stored dry) and in lanes 8 and 9 (stored in A. dest.).

Separation by gel electrophoresis shows high-molecular undegraded DNA both in the lanes which show the reference DNA and in the lanes containing the DNA of the non-stored positive control. Storing the tissue dry or in water leads to total breakdown of the DNA. By contrast, samples treated as in Example 15 remain intact and are undegraded throughout the storage period. Mixtures of tetradecyltrimethyl ammonium oxalate with additives are thus suitable for stabilising DNA in biological samples as well and also allow RNA and DNA to be isolated in parallel from a sample.

The invention claimed is:

1. A nucleic acid storage stabilization composition for stabilizing nucleic acids in a biological sample, said stabilization composition comprising a cationic compound of the general formula:

$$Y^+R_1R_2R_3R_4X^-$$

wherein Y represents nitrogen or phosphorus;

$R_1$, $R_2$, $R_3$ and $R_4$ independently, represent a branched or unbranched $C_1$-$C_{20}$-alkyl group and/or a $C_6$-$C_{20}$-aryl group as well as a $C_6$-$C_{26}$-aralkyl group;

$X^-$ represents an anion of an inorganic or organic, mono- or polybasic acid; and at least one proton donor, wherein the proton donor is present in the composition in a concentration of above 50 mM to saturation and wherein the proton donor is selected from the group consisting of saturated aliphatic monocarboxylic acids, unsaturated alkenyl-carboxylic acids, saturated and/or unsaturated aliphatic $C_2$-$C_6$-dicarboxylic acids, aliphatic hydroxyl-di- and tricarboxylic acids, aliphatic ketocarboxylic acids, amino acids or the inorganic acids or the salts thereof, on their own or in combination.

2. The composition according to claim 1, wherein Y represents nitrogen.

3. The composition according to claim 1, wherein $R_1$ denotes a higher alkyl group with 12, 14 or 16 carbon atoms and $R_2$, $R_3$ and $R_4$ each represent a methyl group.

4. The composition according to claim 1 or 3, wherein the anion $X^-$ represents anions of hydrohalic acids or anions of mono- or dibasic organic acids.

5. The composition according to claim 4, wherein the anion $X^-$ is selected from the group consisting of bromide, chloride, phosphate, sulphate, formate, acetate, propionate, oxalate, malonate, succinate or citrate.

6. The composition according to claim 1, wherein the proton donor is selected from the group consisting of saturated aliphatic monocarboxylic acids, unsaturated alkenyl-carboxylic acids, saturated and/or unsaturated aliphatic $C_2$-$C_6$-dicarboxylic acids, aliphatic ketocarboxylic acids, amino acids or the inorganic acids or the salts thereof, and combinations thereof.

7. The composition according to claim 6, wherein the aliphatic monocarboxylic acid comprises a $C_1$-$C_6$-alkylcarboxylic acid selected from the group consisting of acetic acid, propionic acid, n-butyric acid, n-valeric acid, isovaleric acid, ethyl-methyl-acetic acid (2-methyl-butyric acid), 2,2-dimethylpropionic acid (pivalic acid), n-hexanoic acid, n-octanoic acid, n-decanoic acid or n-dodecanoic acid (lauric acid) or mixtures thereof.

8. The composition according to claim 6, wherein the aliphatic alkenyl-carboxylic acid is selected from the group consisting of acrylic acid (propenoic acid), methacrylic acid, crotonic acid, isocrotonic acid or vinylacetic acid or mixtures thereof.

9. The composition according to claim 6, wherein the saturated aliphatic $C_2$-$C_6$-dicarboxylic acid is selected from the group consisting of oxalic acid, malonic acid, succinic acid, glutaric acid or adipic acid or mixtures thereof.

10. The composition according to claim 9, wherein the aliphatic dicarboxylic acid is oxalic acid or succinic acid or mixtures thereof.

11. The composition according to claim 6, wherein the aliphatic hydroxy-di- and -tricarboxylic acids are selected from the group consisting of tartronic acid, D-(+), L-(−) or DL-malic acid, (2R, 3R)-(+)-tartaric acid, (2S, 3S)-(−)-tartaric acid, meso-tartaric acid and citric acid or mixtures thereof.

12. The composition according to claim 6, wherein the unsaturated dicarboxylic acid is maleic and/or fumaric acid or mixtures thereof.

13. The composition according to claim 6, wherein the unsaturated tricarboxylic acid is aconitic acid.

14. The composition according to claim 6, wherein the aliphatic ketodicarboxylic acids are mesoxalic acid or oxaloacetic acid, or mixtures thereof.

15. The composition according to claim 6, wherein the amino acids are selected from the group consisting of aminoacetic acid (glycine), α-aminopropionic acid (alanine), α-amino-iso-valeric acid (valine), α-amino-iso-caproic acid (leucine) and α-amino-β-methylvaleric acid (isoleucine), or mixtures thereof.

16. The composition according to claim 1, wherein the composition is present in an aqueous solution.

17. The composition according to claim 16, wherein the cationic compound is in a concentration in the range from 0.01 wt. % to 15 wt. %.

18. A method of stabilizing nucleic acids in a biological sample, the method comprising:

mixing a storage stabilization composition with a solution containing the nucleic acids, wherein the composition comprises a cationic compound of the general formula $$Y^+R_1R_2R_3R_4X^-$$

wherein Y represents nitrogen or phosphorus;

$R_1$, $R_2$, $R_3$ and $R_4$, independently, represent a branched or unbranched $C_1$-$C_{20}$-alkyl group and/or a $C_6$-$C_{20}$-aryl group as well as a $C_6$-$C_{26}$-aralkyl group;

$X^-$ represents an anion of an inorganic or organic, mono- or polybasic acid; and at least one proton donor wherein the proton donor is present in the composition in a concentration of above 50 mM to saturation and wherein the proton donor is selected from the group consisting of saturated aliphatic monocarboxylic acids, unsaturated alkenyl-carboxylic acids, saturated and/or unsaturated aliphatic $C_2$-$C_6$-dicarboxylic acids, aliphatic hydroxyl-di- and tricarboxylic acids, aliphatic ketocarboxylic acids, amino acids or the inorganic acids or the salts thereof, on their own or in combination.

19. The method according to claim 18, wherein both ribonucleic acids (RNA) and deoxyribonucleic acids (DNA) are stabilized.

20. The method according to claim 19, wherein ribonucleic acids (RNA) or deoxyribonucleic acids (DNA) in the form of monomeric nucleotides, oligomers, plasmids, in the form of viral and/or bacterial DNA and RNA, as well as genomic and non-genomic DNA and RNA from animal and plant cells or other eukaryotes, are stabilized.

21. The method according to claim 20, wherein mRNA in processed and unprocessed form, tRNA, mRNA, rRNA and cDNA are stabilized.

22. A kit for stabilization of nucleic acids comprising a composition according to claim 1 and instructions for combining said composition with a solution containing nucleic acids to be stabilized.

23. A composition comprising a mixture of a biological sample containing nucleic acid and a composition according to claim 1, optionally together with other excipients.

24. The composition according to claim 23, wherein the pH of the mixture is in the range from 2 to 12.

25. The composition according to claim 23, wherein the biological sample is blood, plasma or serum.

26. The composition according to claim 25, wherein the pH of the mixture is in the range from 2 to 6.

27. The composition according to claim 23, wherein the biological sample is an aspirate, cells, tissue or bacteria.

28. The composition according to claim 27, wherein the pH of the mixture is in the range from 3 to 10.

29. A composition according to claim 25 or 27, wherein the biological sample additionally contains viruses or bacteria.

30. The method according to claim 19, wherein the nucleic acids are stabilized by forming an insoluble ionic complex with the cationic compound.

31. The method according to claim 19, wherein the stabilized nucleic acids are separated from the sample.

32. The method according to claim 30, further comprising the step of separating said insoluble ionic complex from the solution by centrifugation.

33. The method according to claim 30 or 32, further comprising the step of separating said insoluble ionic complex from the solution by filtration.

34. The method according to claim 32, further comprising the step of contacting the centrifuged insoluble ionic complex with a lysing buffer.

35. The method according to claim 30, further comprising the step of analyzing the nucleic acids.

* * * * *